(12) United States Patent
Setoguchi et al.

(10) Patent No.: US 6,428,704 B1
(45) Date of Patent: Aug. 6, 2002

(54) METHOD FOR DETERMINATION OF HEMOGLOBINS

(75) Inventors: Yuji Setoguchi, Shinnanyo; Kazuyuki Oishi; Kazuhiko Shimada, both of Tokuyama; Toshiki Kawabe, Shiga; Takayuki Oka, Osaka, all of (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 09/762,287

(22) PCT Filed: Aug. 4, 1999

(86) PCT No.: PCT/JP99/04202

§ 371 (c)(1),
(2), (4) Date: Feb. 7, 2001

(87) PCT Pub. No.: WO00/08460

PCT Pub. Date: Feb. 17, 2000

(30) Foreign Application Priority Data

Aug. 7, 1998 (JP) .......................... 10-224572
Aug. 7, 1998 (JP) .......................... 10-224573
Aug. 7, 1998 (JP) .......................... 10-224574

(51) Int. Cl.[7] .............................................. B01D 15/08
(52) U.S. Cl. ................ 210/635; 210/656; 210/198.2; 436/66; 436/161; 530/385; 530/413; 530/416; 530/417
(58) Field of Search ................ 210/635, 656, 210/198.2; 530/385, 413, 416, 417; 436/66, 67, 161

(56) References Cited

U.S. PATENT DOCUMENTS 4,168,147 A * 9/1979 Acuff .......................... 210/656
4,647,654 A * 3/1987 Knowles ..................... 530/326
4,658,022 A * 4/1987 Knowles ..................... 530/402
4,727,036 A * 2/1988 Knowles ..................... 436/547
5,432,062 A * 7/1995 Turecek ...................... 435/68.1
5,631,140 A * 5/1997 Kobold ......................... 435/23
5,792,623 A * 8/1998 Turecek ...................... 435/68.1

FOREIGN PATENT DOCUMENTS

| JP | 4-99496 | * | 8/1979 | ................ 210/656 |
| JP | 5-85947 | * | 4/1993 | ................ 210/656 |
| JP | 5-113440 | * | 5/1993 | ................ 210/656 |
| JP | 6-98791 | * | 4/1994 | ................ 210/656 |
| JP | 7-51087 | * | 2/1995 | ................ 210/656 |
| JP | 8-62221 | * | 3/1996 | ................ 210/656 |

OTHER PUBLICATIONS

Japanese patent application laid–open, JP 58–2010665, A Nov. 11, 1983.
Japanese patent application laid–open, JP 1–297554, A Nov. 30, 1989.
Japanese patent application laid–open, JP 5–60742, A Mar. 12, 1993.
Japanese Utility Model application, JP 4–24195 (JP6–7060, A) Jan. 28, 1994.
Japanese patent application laid open, tokuhyouhei 5–508877, A Dec. 9, 1993.

* cited by examiner

*Primary Examiner*—Ernest G. Therkorn
(74) *Attorney, Agent, or Firm*—Townsend & Banta

(57) ABSTRACT

A method for determining hemoglobins is provided which is suitable for determination of stable hemoglobin $A_{1c}$. A method for determining hemoglobins by cation exchange liquid chromatography wherein an eluent is used containing a chaotropic ion and further an inorganic acid, an organic acid and/or any salt thereof having a buffer capacity in the 4.0–6.8 pH range.

11 Claims, 22 Drawing Sheets

(a)

(b)

(c)

(d)

(e)

(f)

(a)

(b)

(a)

(b)

(c)

(a)

(b)

METHOD FOR DETERMINATION OF HEMOGLOBINS

REFERENCE TO RELATED APPLICATIONS

This applications is 317 of PCT/JP99/04202 filed Aug. 4, 1999.

FIELD OF THE INVENTION

This invention relates to a method for determining hemoglobins, specifically directed to determine stable hemoglobin $A_{1c}$ by cation exchange liquid chromatography.

DESCRIPTION OF PRIOR ART

Hemoglobin $A_{1c}$ (hereinafter abbreviated as $HbA_{1c}$) has been frequently listed as a test item in a screening test of diabetes mellitus or as a test item for grasping how well the blood glucose level of diabetics is controlled, because its ratio by composition to all hemoglobins reflects an average blood glucose level (blood glucose concentration) over the preceding 1–2 months.

$HbA_{1c}$ is glycated hemoglobin (hereinafter abbreviated as GHb) produced via a reaction between glucose and hemoglobin A (hereinafter abbreviated as HbA) present in the blood. $HbA_{1c}$, if produced via a reversible reaction therebetween, is called labile $HbA_{1c}$ and, if produced via an irreversible reaction involving the labile $HbA_{1c}$, is called stable $HbA_{1c}$.

Normally, hemoglobin is a tetrameric protein composed of two pairs of two different subunits. HbA has α-chain and β-chain subunits. Binding of glucose to N-terminal amino acid(s) of this/these β-chain results in $HbA_{1c}$. The stable $HbA_{1c}$ better reflects an average blood glucose level over the preceding 1–2 months. In the field of clinical testing, it has been demanded to develop a method whereby the stable $HbA_{1c}$ level (%) can be measured with high precision.

Conventional $HbA_{1c}$ determination methods mostly employ liquid chromatography (hereinafter abbreviated as LC) which, according to a cation exchange technique, separates hemoglobins present in a sample prepared by hemolytically eluting a blood specimen on the basis of difference in positively charged state between hemoglobins (for example, Japanese Patent Publication No. Hei 8-7198).

The separation of hemoglobins present in the hemolyzed sample by means of cation exchange LC, if performed over a sufficiently long period of time, generally results in the sequential elution of hemoglobin $A_{1a}$ (hereinafter abbreviated as $HbA_{1a}$) and hemoglobin $A_{1b}$ (hereinafter abbreviated as $HbA_{1b}$), hemoglobin F (hereinafter abbreviated as HbF), labile $HbA_{1c}$, stable $HbA_{1c}$ and hemoglobin $A_0$ (hereinafter abbreviated as $HbA_0$). $HbA_{1a}$, $HbA_{1b}$ and $HbA_{1c}$ each is GHb in the form of glycated HbA. HbF is fetal hemoglobin composed of α and γ chains. $HbA_0$ consists of a group of hemoglobin components, includes HbA as its primary component and is retained more strongly to a column than $HbA_{1c}$.

The prior techniques have suffered from the following deficiencies: The separation of labile $HbA_{1c}$ from stable $HbA_{1c}$ is insufficient; and "modified hemoglonins", such as acetylated hemoglobin (hereinafter abbreviated as AHb) and carbamylated hemoglobin (hereinafter abbreviated as CHb), are eluted together with stable $HbA_{1c}$.

That is, in the determination of hemoglobins present in a blood sample, primarily purposed to measure a stable $HbA_{1c}$ level (%) by cation exchange LC, it has been difficult to separate labile $HbA_{1c}$, AHb and CHb peaks from a stable $HbA_{1c}$ without affecting measurement of stable $HbA_{1c}$ level, since their elution behaviors resemble each other.

Hemoglobin S (hereinafter abbreviated as HbS) and hemoglobin C (hereinafter abbreviated as HbC) are known as "abnormal hemoglobins". HbS and HbC result from substitution of glutamic acid located in a sixth position from an N-terminal of the β chain of HbA for valine and lysine, respectively.

Hemoglobin $A_2$ (hereinafter abbreviated as $HbA_2$) is composed of α and δ chains and, like HbF, its elevated level is interpreted as evidence of Mediterranean anemia (thalassemia).

In the normal determination of hemoglobins by cation exchange LC, they are eluted in the sequence of $HbA_0$, $HbA_2$, HbS and HbC.

In the determination of stable $HbA_{1c}$ present in a specimen which also contains HbS, HbC or other abnormal hemoglobins, it is required that peaks of these hemoglonins be separated from a $HbA_0$ peak and that the stable $HbA_{1c}$ level (%) be determined by calculating a ratio of a peak area of stable $HbA_{1c}$ to a total peak area of hemoglobin components exclusive of abnormal hemoglobins.

When the simultaneous examination of Mediterranean anemia is desired, an elustion condition is established that allows separation of $HbA_2$ from $HbA_0$. In this case, the ratio in level of HbF and $HbA_2$ to all hemoglobins is calculated to provide measurement result.

In the normal separation of hemoglobins by means of cation exchange LC, the hemoglobin components included in the $HbA_0$ peak (hereinafter abbreviated as $HbA_0$ components) are classified into the following two cases depending upon the measurement conditions used. Under the measurement condition where a blood specimen containing $HbA_2$, abnormal hemoglobins or the like which tend to become retained more strongly by packing materials than HbA is subjected to a single-step elution, a resulting peak includes not only HbA but also those hemoglobin components. On the other hand, under the measurement condition that effects separation of $HbA_2$, abnormal hemoglobins and the like, a peak primarily of HbA results.

A typical LC used in the determination of Hb's is cation exchange LC (for example, Japanese Patent Publication No. Hei 8-7198).

Examples of packing materials known to be useful for determination of hemoglobins include those made via a reaction of inorganic or organic polymer particles with a compound having an ion exchange group, and those made via polymerization of a monomer having an ion exchange group with a crosslinking monomer.

One of important factors that determine performances of such cation-exchange packing materials is the ion exchange capacity. Conventional cation-exchange packing materials have ion exchange capacities in the approximate range of several meq–several tens meq/g, 0.2–0.3 meq/g at the lowest. The ion exchange capacity depends not only upon the amount of the ion exchange group-containing compound to be reacted and the condition under which it is reacted, but also upon the particle size, specific surface area, pore size, pore volume and the like of the packing material used. It is thus considered very important to achieve simultaneous optimization of ion exchange capacity, pore size, specific surface area, pore volume and the like for the sake of precise separation.

Japanese Patent Laying-Open No. Hei 7-27754 discloses reacting porous particles having pore diameters in the range of 20–2,000 angstroms and specific surface areas of 0.1–100 $m^2/g$ with ion exchange group-containing compounds to thereby obtain packing materials having ion exchange capacities in the range of 0.5–3.0 meq/g.

The packing materials described in this reference are obtained by reacting polymeric particles and the like with ion exchange group-containing compounds. Accordingly, it has been difficult to introduce a controlled amount of ion exchange group-containing compounds into the polymeric particles and the like. The problem of poor reproducibility thus remains (Yoshimawari, Hosoya, Kimata and Tanaka; Chromatography, vol.16(1), pp. 7–12 (1995)).

Also, in the case where the polymeric particles are silica particles, the following problems arise: a pH range of an eluent is limited; resolution is reduced by non-specific adsorption; and service lives of columns are shortened. In the case of natural polymeric particles which show the increased tendency to swell and shrink, a problem of low pressure resistance arises.

On the other hand, the packing materials made via polymerization of an ion exchange group-containing monomer with a crosslinking monomer appear to be favored over the above-described packing materials since their use increases reproducibility, eases manufacture and extends service lives of columns. However, packing materials are not yet reported which result from polymerization of an ion exchange group-containing monomer with a crosslinking monomers and have optimized pore size, specific surface area, pore volume, ion exchange capacity and the like.

A high-performance liquid chromatography (hereinafter abbreviated as HPLC) specially designed to use columns packed with the above-described conventional materials have come into spread use as an "automatic glycated hemoglobin measurement device" in the field of clinical testing.

Such devices generally utilize cation exchange as a separating mechanism, and separates hemoglobins based on the difference in degree of interaction between positive charges thereon and negative charges on the functional groups introduced in the packing materials.

A special eluent for use in such a device is generally prepared by adding sodium chloride or the like, as an ionic strength adjusting agent, to a phosphate or other buffer which exhibits a buffering action under a more acidic condition than an isoelectric point so that each hemoglobin component becomes positively charged.

Generally, a single liquid delivery pump is used to deliver 2 or 3 types of eluents having different elution powers according to a stepwise gradient elution technique. The control of pH and ioninc strength creates such a difference in elution power between the eluents.

Where two types of eluents are used, a first eluent having a weaker elution power is initially delivered to elute from $HbA_{1a}$ to $HbA_{1c}$ and subsequently changed to a second eluent having a stronger elution power for elution of $HbA_0$. Where three types of eluents are used, a first eluent having the weakest elution power is initially used to elute from $HbA_{1a}$ to the vicinity of HbF, subsequently changed to a second eluent having a stronger elution power to elute therefrom to $HbA_{1c}$, and finally changed to a third eluent having the strongest elution power to elute remaining hemoglobin components, i.e., $HbA_0$ and followers. The use of three different eluents complicates the device, but provides a sharper $HbA_{1c}$ peak and permits shortening of a measuring time.

Before a sample is poured into an HPLC, blood must be pretreated with a hemolyzing reagent (hemolytically diluting liquid) which desirably hemolytically dilutes the blood to a suitable hemoglobin concentration without adverse effect on separation. A typical reagent is thus prepared by adding a hemolyzing agent, such as a nonionic surface active agent, to a liquid buffer incorporating the same buffering agent as contained in the eluent.

Such a device generally includes a line filter upstream of a column to prevent the "fragments" of sealing medium of the liquid delivery pump or foreign substances present in the sample from entering the columns. During measurement, the line filter shows an increasing pressure loss with accumulation of foreign substances, which is associated with the pressure resistance or the like of the device. This necessitates replacement of the line filter. Since a replacing operation of the line filter requires a labor hour, a measure to extend a service life of the line filter is demanded to improve handling characteristics of the device.

Another filter (hereinafter referred to as a column filter) is provided within an end fitting disposed in each end of a column to accommodate packing materials within the column while permitting flow of the eluent and sample through the column.

These line and column filters are generally required that their material type and configuration should not adversely affect the separation of components to be determined. Typically, they are constructed from stainless steel and have a cylindrical configuration.

SUMMARY OF THE INVENTION

It is an object of the present invention to provide a method for determining hemoglobins which can overcome the above-described dificiecies encountered in the prior techniques, which provides a satisfactory resolution within a short period of time and which enables determination of stable $HbA_{1c}$ with high precision.

It is a further object of the present invention to provide a packing material for cation exchange LC which can overcome the above-described dificiecies encountered in the prior packing materials for cation exchange LC, which exhibits satisfactory durability and reproducibility, and which permits a high resolution within a short period of time.

In accordance with a first invention of the present application, a method for determining hemoglobins by cation exchange LC is provided which characteristically employs an eluent which contains a chaotropic ion and also contains an inorganic acid, an organic acid and/or any salt thereof having a buffer capacity in the 4.0–6.8 pH range.

In accordance with a second invention of the present application, a method for determining hemoglobins by cation exchange LC is provided which characteristically employs an eluent which contains a chaotropic ion and also contains a buffer agent having acid dissociation constants (pKa) in the range of 2.15–6.39 and in the range of 6.40–10.50.

In a particular aspect of the present invention, an eluent is employed which, when entering a column, has a pH equal to or shifted to an alkaline side than an isoelectric point of hemoglobin so that $HbA_0$ can be eluted.

In a more particular aspect of the present invention, the eluent has a pH of 6.8 or higher.

In a further particular aspect of the present invention, at least 3 types of eluents having different elution powers are used. Before one type of eluent purposed to elute $HbA_0$ is delivered, the other types of eluents are delivered.

In a particular aspect of the present invention, an eluent is delivered according to a linear gradient or stepwise gradient elution technique and its elution power is reduced in the course of delivering.

In a further particular aspect of the present invention, subsequent to elution of $HbA_0$, at least one type of hemoglobin from the group consisting of $HbA_2$, HbS and HbC is eluted.

In a further particular aspect of the present invention, the aforementioned eluent contains one or more types of amines having a molecular weight of 20–500.

In a further particular aspect of the present invention, a hemolyzing reagent is used containing one or more types of amines having a molecular weight of 20–500.

The LC packing material according to the present invention is the LC packing material for cation exchange chromatography applicable to the method of determining hemoglobins according to the present invention, and is characterized by the followings: it is comprised of a polymer formed from a monomer having an ion exchange group and a crosslinking monomer; it has pores having an average diameter of 10–100 angstroms; and it has a specific surface area of 0.05–5 $m^2$ per unit dry weight (1 g) of the packing material, a pore volume of 0.1–10 $\mu$L per unit driy weight (1 g) of the packing material and an ion exchange capacity of 1–100 $\mu$eq per unit dry weight (1 g) of the packing material.

A filter applicable to the method for determining hemoglobins in accordance with the present invention is characterized as being comprised of polyether ketone and/or polyethylene.

A hemolyzing reagent for use in the hemolysis of a blood specimen in the method for determining hemoglobins according to the present invention is characterized as containing a chaotropic ion.

The present invention is below explained in detail.

(First Invention)

The eluent used in the first invention of the present application contains a chaotropic ion, and also contains an inorganic acid, an organic acid or any salt thereof having a buffer capacity in the 4.0–6.8 pH range.

The chaotropic ion is an ion which is produced via dissociation of compounds when dissolved in an aqueous solution, destroys a structure of water and suppresses the entropy reduction of water that occurs upon contact with a hydrophobic material.

Examples of negative chaotropic ions include a tribromo acetate ion, trichloroacetate ion, thiocyanate ion, iodide ion, perchlorate ion, dichloroacetate ion, nitrate ion, bromide ion, chloride ion, acetate ion and the like. Examples of positive chaotropic ions include a barium ion, calcium ion, lithium ion, cesium ion, potassium ion, magnesium ion, guanidine ion and the like.

Preferred chaotropic ions which can be used in the first invention, among the above-listed ions, include such negative ions as a tribromoacetate ion, trichloroacetate ion, thiocyanate ion, iodide ion, perchlorate ion, dichloroacetate ion, nitrate ion and bromide ion; and such positive ions as a barium ion, calcium ion, magnesium ion, lithium ion, cesium ion and guanidine ion. More preferred are a thiocyanate ion, perchlorate ion, nitrate ion and guanidine ion.

If a concentration of the chaotropic ion present in the eluent is below 0.1 mM, a separating effect may be reduced in the determination of homoglobins. On the other hand, if it exceeds 3000 mM, the effect of separating hemoglobins shows no further improvement. Therefore, the chaotropic ion is incorporated in the eluent in a concentration preferably of 0.1 mM–3,000 mM, more preferably of 1 mM–1,000 mM, most preferably of 10 mM–500 mM.

Also, the above-listed chaotropic ions may be used in combination.

The chaotropic ion may be incorporated in a liquid to be contacted with a sample subject to determination, such as a hemolyzing reagent, sample diluting liquid or the like.

In the first invention, a substance having a buffer capacity, i.e., an inorganic acid, organic acid or any salt thereof, is incorporated in the eluent. Examples of inorganic acids include carbonic acid, phosphoric acid and the like. Examples of organic acids include carboxylic acid, dicarboxylic acid, carboxylic acid derivatives, hydroxycarboxylic acid, amino acid, cacodylic acid, pyrophosphoric acid and the like.

Examples of carboxylic acids include acetic acid, propionic acid and the like. Examples of dicarboxylic acids include malonic acid, succinic acid, glutaric acid, adipic acid, maleic acid, fumaric acid, phthalic acid and the like. Examples of carboxylic acid derivatives include β,β-dimethyl glutaric acid, barbituric acid, aminobutyric acid and the like. Examples of hydroxycarboxylic acids include citric acid, tartaric acid, lactic acid and the like. Examples of amino acids include aspartic acid, asparagine and the like.

The salts of inorganic and organic acids are known in the art and include sodium salts and potassium salts, for example.

The above-listed inorganic acids, organic acids and salts thereof may be used in any combination. Also, the above-listed inorganic acids and organic acids may be used in combination.

Where the above-listed inorganic acids, organic acids and/or salts thereof are used in combination, a total concentration of the combination is adjusted to a level sufficient to buffer the eluent at a pH of 4.0–6.8, preferably to 1–1,000 mM, more preferably to 10–500 mM.

In the first invention, the eluent pH is maintained within the range of 4.0–6.8, preferably within the range of 4.5–5.8. If the eluent pH falls below 4, denaturation of hemoglobins may be caused to occur. On the other hand, if the eluent pH exceeds 6.8, hemoglobins may be charged less positively to be less retained by the cation exchange group. This results in poor separation of hemoglobins.

The following substances may be incorporated in the eluent.

(1) Inorganic salts (sodium chloride, potassium chloride, sodium sulfate, potassium sulfate, sodium phosphate and the like) may be added. While not limiting, these salts may preferably be added in concentrations of 1–1,500 mM.

(2) Known acids or bases may be added as pH adjustors. Examples of such acids include hydrochloric acid, phosphoric acid, nitric acid, sulfuric acid and the like. Examples of such bases include sodium hydroxide, potassium hydroxide, lithium hydroxide, magnesium hydroxide, barium hydroxide, calcium hydroxide and the like. While not limiting, these acids or bases may preferably be added in concentrations of 0.001–500 mM.

(3) Water-soluble organic solvents, such as methanol, ethanol, acetonitrile and acetone, may be mixed. Although not limiting, these organic solvents may preferably be added in concentrations of 0–80% (v/v). Preferably, they may be used in concentration levels that do not cause deposition of the chaotropic ion, inorganic acid, organic acid and any salt thereof incorporated.

(4) Preservatives, such as sodium azide and thymol, may be added.

(5) As substances for stabilizing hemoglobins, known stabilizers may be added including chelating agents, such as ethylenediaminetetraacetic acid (EDTA), and reducing agents/antioxidants such as glutathione and sodium azide.

(Second Invention)

In the second invention of the present application, the eluent is used which contains the aforementioned chaotropic ion and a buffering agent having acid dissociation constants (pKa) in the range of 2.15–6.39 and in the range of 6.40–10.50. Since the type, concentration and other details of the chaotropic ion used in the second invention are similar to the case of first invention, their descriptions are omitted here by referring to those given in explaining the chaotropic ion in the first invention.

The buffering agent used in the second invention has acid dissociation constants (pKa) in the range of 2.15–6.39 and in the range of 6.40–10 50. For the buffering agent, a single substance may be used which has at least one pKa value in the range of 2.15–6.39 and at least one pKa value in the range of 6.40–10 50. Alternatively, a substance having at least one pKa value in the range of 2.15–6.39 may be combined with another substance having at least one pKa value in the range of 6.40–10.50. Those buffering agents may be used in combination.

The buffering agent preferably has pKa values in the range of 2.61–6.39 and in the range of 6.40–10.50, more preferably in the range of 2.80–6.35 and in the range of 6.80–10.00, most preferably in the range of 3.50–6.25 and in the range of 7.00–9.50. The buffering agent having pKa values within such-specified ranges shows the improved buffer capacity in the neighborhood of eluent's pH suitable for separation of target peaks.

Examples of buffering agents include inorganic substances such as phosphoric acid, boric acid, carbonic acid and the like; and organic substances such as caboxylic acids, dicarboxylic acids, carboxylic acid derivatives, hydroxycarboxylic acids, aniline or aniline derivatives, amino acids, amines, imidazoles, alcohols and the like. Other useful organic substances include, for example, ethylenediaminetetraacetic acid, pyrophosphoric acid, pyridine, cacodylic acid, glycerol phosphate, 2,4,6-collidine, N-ethylmorpholine, morpholine, 4-aminopyridine, ammonia, ephedrine, hydroxyproline, perydine, tris(hydroxymethyl)aminomethane and glycylglycine.

Examples of carboxylic acids include acetic acid, propionic acid, bezoic acid and the like.

Examples of dicarboxylic acids include malonic acid, succinic acid, glutaric acid, adipic acid, maleic acid, fumaric acid, phthalic acid and the like.

Examples of carboxylic acid derivatives include β,β-dimethyl glutaric acid, barbituric acid, 5,5-diethyl barbituric acid, γ-aminobutyric acid, pyruvic acid, furancarboxylic acid, e-aminocaproic acid and the like.

Examples of hydroxycarboxylic acids include tartaric acid, citric acid, lactic acid, malic acid and the like.

Examples of aniline or aniline derivatives include aniline, dimethylaniline and the like.

Examples of amino acides include aspartic acid, asparagine, glycine, α-alanine, β-alanine, histidine, serine, leucine and the like. Examples of amines include ethylenediamine, ethanolamine, trimethylamine, diethanolamine and the like. Examples of imidazoles include imidazole, 5(4)-hydroxyimidazole, 5(4)-methylimidazole, 2,5(4)-dimethylimidazole and the like.

Examples of alcohols include 2-amino-2-methyl-1,3-propanediol, 2-amino-2-ethyl-1,3-propanediol, 2-amino-2-methyl-1-propanol and the like.

Examples of buffering agents include 2-(N-morpholino)ethanesulfonic acid (MES), bis(2-hydroxyethyl)iminotris-(hydoxylmethyl)methane (Bistris), N-(2-acetamido)iminodiacetic acid (ADA), piperazine-N,N'-bis(2-ethanesulfonic acid) (PIPES), 1,3-bis(tris(hydoxymethyl)methylamino) propane (Bistrispropane), N-(2-acetamide)-2-aminoethanesulfonic acid (ACES), 3-(N-morpholine)propanesulfonic acid (MOPS), N,N'-bis(2-hydroxyethyl)-2-aminoethanesulfonic acid (BES), N-tris(hydroxymethyl)methyl-2-aminoethanesulfonic acid (TES), N-2-hydroxyethylpiperazine-N'-2-ethanesulfonic acid (HEPES), N-2-hydroxyethylpiperazine-N'-2-propanesulfonic acid (HEPPS), N-tris(hydroxymethyl)methylglycine (Tricine), tris(hydroxymethyl)aminoethane (Tris), N,N'-bis(2-hydroxyethyl)glycine (Bicine), glycylglycine, N-tris(hydroxymethyl)methyl-3-aminopropanesulfonic acid (TAPS), glycine, cyclohexylamino-propanesulfonic acid (CAPS) and the like, which generally constitute a Good's buffer. The pKa values of these substances are shown in Tables 1 and 2 (cited reference: Takeichi HORIO and Nihei YAMASHITA, Fundamental Experimental Procedures of Proteins and Enzymes, Nanko-do (1985)).

TABLE 1

| Buffer | x | pKax | °C. |
|---|---|---|---|
| Oxalic Acid | 1 | 1.27 | 25 |
| | 2 | 4.27 | |
| Ethylenediamin-etetraacetic Acid | 1 | 1.7 | 20 |
| | 2 | 2.6 | |
| | 3 | 6.3 | |
| | 4 | 10.6 | |
| Maleic Acid | 1 | 1.92 | 20 |
| | 2 | 6.23 | |
| Aspartic Acid | 1 | 1.99 | 25 |
| | 2 | 3.90 | |
| | 3 | 10.00 | |
| Phosphoric Acid | 1 | 2.15 | 25 |
| | 2 | 7.20 | |
| | 3 | 12.38 | |
| Asparagine | 1 | 2.1 | 25 |
| | 2 | 8.8 | |
| Glycine | 1 | 3.52 | 20 |
| | 2 | 9.91 | |
| Pyruvic Acid | 1 | 2.60 | 25 |
| Pyrophosphoric Acid | 2 | 2.0 | 25 |
| | 4 | 8.95 | |
| Malonic Acid | 1 | 2.85 | 25 |
| | 2 | 5.70 | |
| Phthalic Acid | 1 | 2.95 | 25 |
| | 2 | 5.41 | |
| Fumaric Acid | 1 | 3.10 | 25 |
| | 2 | 4.38 | |
| Tartaric Acid | 1 | 3.04 | 25 |
| | 2 | 4.37 | |
| Citric Acid | 1 | 3.13 | 25 |
| | 2 | 4.76 | |
| | 3 | 6.40 | |
| Furancarboxylic Acid | 1 | 3.17 | 25 |
| β-Alanine | 1 | 3.55 | 25 |
| | 2 | 10.24 | |
| β,β-Dimethyl-glutaraic Acid | 1 | 3.71 | 25 |
| | 2 | 6.34 | |
| Formic Acid | 1 | 3.75 | 25 |
| Lactic Acid | 1 | 3.86 | 25 |
| γ-Aminobutyric Acid | 1 | 4.03 | 25 |
| | 2 | 10.56 | |

TABLE 1-continued

| Buffer | x | pKax | °C. |
|---|---|---|---|
| barbituric Acid | 1 | 4.04 | 25 |
| Benzoic Acid | 1 | 4.20 | 25 |
| Succinic Acid | 1 | 4.21 | 25 |
|  | 2 | 5.64 |  |
| ε-Aminocaproic Acid | 1 | 4.38 | 20 |
|  | 2 | 10.98 |  |
| Acetic Acid | 1 | 4.76 | 25 |
| Propionic Acid | 1 | 4.87 | 25 |
| Malic Acid | 1 | 5.26 | 25 |
| Pyridine | 1 | 5.17 | 25 |
| Histidine | 2 | 6.04 | 25 |
| Cacodylic Acid | 1 | 6.27 | 25 |
| 5(4)-Hydoxyimidazole | 1 | 6.39 | 25 |

TABLE 2

| Buffer | x | pKax | °C. |
|---|---|---|---|
| Carbonic Acid | 1 | 3.76 | 27 |
|  | 2 | 10.33 | 25 |
| Glycerol Phosphate | 2 | 6.65 | 25 |
| Ethylenediamine | 1 | 6.85 | 25 |
|  | 2 | 9.91 |  |
| Imidazole | 1 | 6.95 | 25 |
| Arsenic Acid | 2 | 6.77 | 25 |
| 2,4,6-Collidine | 1 | 7.43 | 25 |
| 5(4)-Methylimidazole | 1 | 7.52 | 25 |
| N-Ethylmorpholine | 1 | 7.67 | 25 |
| 5,5-Diethyl-barbituric Acid | 1 | 7.98 | 25 |
| 2,5(4)-Dimethylimidazole | 1 | 8.36 | 25 |
| Morpholine | 1 | 8.60 | 25 |
| 2-Amino-2-Methyl-1,3-Propanediol | 1 | 8.79 | 25 |
| 2-Amino-2-Ethyl-1,3-Propanediol | 1 | 8.80 | 25 |
| Diethanolamine | 1 | 8.88 | 25 |
| 4-Aminopyridine | 1 | 9.11 | 25 |
| Serine | 2 | 9.21 | 25 |
| Boric Acid | 1 | 9.24 | 25 |
| Ammonia | 1 | 9.25 | 25 |
| Ethanolamine | 1 | 9.50 | 25 |
| Ephedrine | 1 | 9.39 | 25 |
| Hydroxyproline | 2 | 9.66 | 25 |
| 2-Amino-2-Methyl-1-Propanol | 1 | 9.69 | 25 |
| Leucine | 2 | 9.74 | 25 |
| Trimethylamine | 1 | 9.80 | 25 |
| α-Alanine | 1 | 9.87 | 25 |
| n-Propyl Alcohol | 1 | 10.57 | 25 |
| Methylamine | 1 | 10.64 | 25 |
| Ethylamine | 1 | 10.63 | 25 |
| n-Butylamine | 1 | 10.64 | 25 |
| Triethylamine | 1 | 10.72 | 25 |
| Dimethylamine | 1 | 10.77 | 25 |
| Hexamethylene-diamine | 2 | 10.93 | 25 |
| Piperidine | 1 | 11.12 | 25 |
| MES | 1 | 6.15 | 20 |
| Bistris | 1 | 6.5 | 20 |
| ADA | 1 | 6.6 | 20 |
| PIPES | 1 | 6.8 | 20 |
| Bistrispropane | 1 | 6.8 | 20 |
|  | 2 | 9.0 |  |
| ACES | 1 | 6.9 | 20 |
| MOPS | 1 | 7.15 | 20 |
| BES | 1 | 7.15 | 20 |
| TES | 1 | 7.5 | 20 |
| HEPES | 1 | 7.55 | 20 |
| HEPPS | 1 | 8.1 | 20 |
| Tricine | 1 | 8.15 | 20 |
| Tris | 1 | 8.3 | 20 |
| Bicine | 1 | 8.35 | 20 |
| Glycylglycine | 1 | 8.4 | 20 |
| TAPS | 1 | 8.55 | 20 |
| Glycine | 1 | 9.9 | 20 |
| CAPS | 1 | 10.4 | 20 |

The concentration of the buffering agent in the eluent is not particularly specified, so long as its buffer action is effective. It is preferably in the range of 1–1,000 mM, more preferably in the range of 10–500 mM. The above-listed buffering agents may be used alone or in combination. For example, organic and inorganic buffering agents may be used in combination.

In the method of determining hemoglobins according to the second invention, an inorganic salt, pH adjusting agent, water-soluble organic solvent, sodium azide or hemoglobin stabilizer may be incorporated in the eluent, as similar to the case of first invention.

In the present invention, at least two types of eluents having different pH values may preferably be used. In such a case, the eluents used to separate target peaks preferably contain the same type of buffering agent. However, such is not necessary unless measurements are adversely affected by a baseline variation (of detector output) that may occur when the eluents are changed from one to another.

Preferably, the eluents used to separate target peaks contain the same concentration of buffering agent. This is effective to further reduce the baseline variation.

The pH's of the eluents can be controlled by the amount of the pH adjustor to be added thereto.

At least two types of eluents having differring pH's may be delivered according to a gradient or stepwise gradient elution technique.

The target peaks, as described above, include $HbA_{1a}$, $HbA_{1b}$, HbF, labile $HbA_{1c}$, stable $HbA_{1c}$, AHb, CHb, $HbA_0$, $HbA_2$, HbS, HbC and the like.

The pH of the eluent used to separate hemoglobin components to be eluted earlier than $HbA_0$ is preferably kept in the range of 4.0–6.8, more preferably in the range of 4.5–5.8. If the pH falls below 4.0, modification of hemoglobins may be caused to occur. If the pH exceeds 6.8, hemoglobins may be charged less positively to be less retained by the cation exchange group. This results in poor resolution.

In the present invention, in order to elute $HbA_0$, i.e., "$HbA_0$ components" consisting of HbA and others which are retained more strongly by the packing material than $HbA_{1c}$, the eluent is preferably adjusted such that it, when enters a column, has a pH equal to or shifted toward an alkaline side than an isoelectric point of hemoglobin. Such a condition is attainable by various techniques, such as the delivery of one eluent that has a pH shifted to an alkaline side than an isoelectric point of hemoglobin, and the use of at least two eluents having different pH's.

When the eluent pH is shifted from an acidic side to an alkaline side than an isoelectric point of hemoglobin, a total charge of the hemoglobin is changed from positive to negative. This results in "elution of $HbA_0$ components by the action of an electrical repulsive force" with respect to the cation exchange group incorporated in the packing material.

The isoelectric point of hemoglobin exists in the 6.8–7.0 pH range, as described in the Encyclopedia of Physics and Chemistry (page 1178, 4th ed., Iwanami Shoten, September 1987, edited by Ryogo Kubo et al.). Accordingly, it is more preferred that the eluent, when enters a column, has a pH of 6.8 or higher, for the purpose of eluting $HbA_0$ components.

If such a condition is to be satisfied, at least one of the eluents used must have a pH of 6.8 or higher. Such an eluent preferably has a pH of 7.0–12.0, more preferably of 7.5–11.0, most preferably of 8.0–9.5. If the pH of this eluent is below 6.8, insufficient elution of $HbA_0$ components may result. The eluent pH is preferably adjusted within the range that does not cause decomposition of the packing material used.

Examples of eluents suitable for elution of $HbA_0$ components, i.e., having buffering capacities at a pH of 6.8 or higher, include buffers comprised of inorganic acids, organic acids and salts thereof. Examples of inorganic acids include phosphoric acid, boric acid, carbonic acid and the like. Examples of organic acids include hydroxycarboxylic acids such as citric acid, caboxylic acid derevatives such as $\beta,\beta$-dimethylglutaric acid, dicarboxylic acids such as maleic acid, cacodylic acid and the like. Also useful are so-called Good's buffers, examples of which include 2-(N-morpholino) ethanesulfonic acid (MES), N-2-hydroxyethylpiperazine-N'-2-ethanesulfonic acid (HEPES), bis(2-hydroxyethyl)iminotris-(hydoxylmethyl)-methane (Bistris), Tris, ADA, PIPES, Bistris propane, ACES, MOPS, BES, TES, HEPPS, Tricine, Bicine, glycylglycine, TAPS, CAPS and the like. Also useful are a Britton and Robinson's buffer and a GTA buffer. Organics can also be used which include imidazoles such as imidazole; amines such as ethylenediamine, methylamine, ethylamine, triethylamine, diethanolamine, triethanolamine; amino acids such as glycine, $\beta$-alanine, aspartic acid, asparagine; and the like.

The above-listed inorganic acids; organic acids; salts of those inorganic and organic acids; and organics may be used in combination. Alternatively, the above-listed organic acids, inorganic acids and organics may be used in combination.

Preferably, a chaotropic ion is incorporated in the eluent to achieve more effective elution of $HbA_0$ components. The type and other details of the chaotropic ion are similar to the case of first invention.

The chaotropic ion is added in the concentration of 1–3,000 mM, preferably of 10–1,000 mM, more preferably of 50– 500 mM.

In a particular aspect of the present invention, three types of eluents having different elution powers are used. Before one type of eluent purposed to elute $HbA_0$ is delivered, the other types of eluents are delivered.

That is, when the eluent purposed to elute $HbA_0$ components are passed through a column (by a delivery pump), the $HbA_0$ components are eluted. Before this eluent is delivered, the other types of eluents are delivered so that the other hemoglobin components are eluted earlier than $HbA_0$ components.

Target peaks such as stable $HbA_{1c}$ can be eluted more sharply if at least two eluents having a pH of 4.0–6.8 are used to elute the other hemoglobin components earlier than $HbA_0$ components according to a salt concentration gradient technique, a pH gradient technique or combination thereof.

In a particular aspect of the present invention, at least two eluents are used to elute hemoglobins ($HbA_{1a}$, $HbA_{1b}$, HbF, labile $HbA_{1c}$, stable $HbA_{1c}$) earlier than $HbA_0$ and one eluent having the weakest elution power is delivered earliest of all.

In the method for determining hemoglobins according to the present invention, an eluent may preferably be delivered according to a linear gradient or stepwise gradient elution technique with its elution power being reduced along the delivery path.

Conventional LC methods utilize a linear gradient or stepwise gradient elution techniuque using plural eluents, whereby peaks of components subject to separation are sharpened and the resolution of neighboring two or more elution peaks is improved.

The so-called "linear gradient elution technique" employs plural delivery pumps by which delivery ratios of plural eluents having different elution powers are continuously changed. As a result, elution proceeds such that an overall elution power increases continuously with time, as shown in FIG. 32.

The so-called "stepwise gradient elution technique" employs one delivery pump communicatively connected to plural eluents as by a solenoid valve. The sequence of delivery is varied from the eluent having a lower elution power to the eluent having a higher elution power by changing a position of the solenoid valve. As a result, the elution power shows a stepwise increase as shown in FIG. 33.

However, in the case where components to be eluted are similar in nature to each other or where elution must be performed within a short period of time, the conventional gradient or stepwise gradient elution technique carries a possibility that peaks of similar components are overlaid by each other to result in the reduced resolution.

In contrast, in the above-described particular aspect of the present invention, while the series of eluents are delivered according to the gradient or stepwise elution process, their delivery sequence is controlled such that the elution power is temporarily reduced along a deliverty path, considering peaks subject to separation or timing of elution between the peaks, to sharpen and improve resolution of the peaks. Specifically where the stepwise elution process is utilized, the eluents are sequentially delivered in the following fashion; the eluent having a lower elution power is initially delivered, changed to the eluent having a higher elution power, then to the eluent having a lower elution power, and after a while, finally to the eluent having a higher elution power.

In the cation exchange LC, the elution power of the eluent can be reduced, for example, by a technique whereby a salt concentration of the eluent is lowered, a technique whereby a pH of the eluent is lowered, or a combination thereof.

In the anion exchange LC, a technique may be utilized which lowers a salt concentration of the eluent or increases a pH of the eluent. In the reversed phase chromatography,. a technique may be utilized whereby the polarity of an organic solvent is elevated. In the normal phase chromatography, a technique may be utilized whereby the polarity of an organic solvent is lowered.

The followings more specifically illustrate the case where hemoglobins are separated according to a technique whereby the elution power of the eluent is lowered while it is delivered according to a gradient or stepwise elution process.

For the separation of hemoglobins, a column packed with cation-exchange materials is used. An eluent having a salt concentration of 20–1,000 mM and a pH in the range of 4–9 is delivered according to a gradient or stepwise elution process. The eluent while delivered is reduced to a salt concentration of 5–500 mM and a pH in the range of 0.1–3, so that its elution power is lowered along a delivery path.

FIG. 16 shows an exemplary equipment by which the method of the present invention can be practiced according to the stepwise elution process. Eluents A, B, C and D have different elution powers (e.g., differing from each other in salt concentration, pH, polarity or the like). A solenoid valve 1 controls a selective delivery of such eluents at specified time intervals. The selected eluent, together with a sample introduced from a sample injector 3, are supplied to the column 4 by a delivery pump 2. Hemoglobin components present in the sample are detected by a detector 5. An integrator 6 caluculates an area, height and other characteristic values of each peak.

In the case where a blood sample is analyzed containing hemoglobin components, such as $HbA_2$, HbS and HbC, that could adversely affect determination of stable $HbA_{1c}$, a procedure whereby HbA is primarily eluted as a representative $HbA_0$ component (peak) may be put to precede a procedure whereby $HbA_2$, HbS, HbC and the like are eluted. This enables the separation of hemoglobin components other than HbA from the $HbA_0$ peak, leading to more precise calculation of stable $HbA_{1c}$ (%)

In the case where the procedure of eluting $HbA_2$, HbS, HbC and the like is established, the "eluent purposed to elute $HbA_0$", as used in the above-described method where at least three types of eluents are used having different elution powers, means an eluent purposed to elute $HbA_0$ peak consisting primarily of HbA. It is then required to deliver an eluent having a stronger elution power to elute $HbA_2$, HbS, HbC and the like after the "eluent purposed to elute $HbA_0$" has been delivered.

In the present method for determining hemoglobins by cation exchange LC, in the case where the hemoglobins may affect measurements by their adsorption to a flow passage, at least one type of amine having a molecular weight of 20–500 is preferably incorporated in the eluent or hemolyzing reagent according to the present invention.

Examples of such amines include primary, secondary and tertiary amines having melecular weights of 20–500. Examples of primary amines include methylamine, ethylamine, 2-aminoethanol and the like. Examples of secondary amines include dimethylamine, diethylamine, ethylmethylamine and the like. Examples of tertiary amines include trimethylamine, triethylamine, dimethylethylamine and the like.

The amine, if its molecular weight falls below 20, becomes highly volatile to present a storage problem. The amine becomes less soluble if its molecular weight exceeds 500. Accordingly, the molecular weight of the amine is maintained within the range of 20–500, preferably 25–400, more preferably 30–150.

If the concentration of the amine incorporated in the eluent or hemolyzing reagent is below 1 ppm, nonspecific adsorption of hemoglobins is likely to occur within a flow path. If it exceeds 5,000 ppm, poor resolution of hemoglobins result. Accordingly, the amine concentration is preferably maintained in the range of 1–5,000 ppm, more preferably 5–1,000 ppm, most preferably 10–500 ppm.

The packing material for use in the determination of Hb's in accordance with the present invention is the packing material for cation exchange LC, which comprises a polymeric material derived from a monomer having a cation exchange group and a crosslinking monomer. The packing material has pores having an average diameter of 10–100 angstroms, a specific surface area of 0.05–5 $m^2$ per unit dry weight (1 g) of the packing material, a pore volume of 0.1–10 $\mu L$ per unit dry weight (1 g) of the packing material and an ion exchange capacity of 1–100 $\mu eq$ per unit dry weight (1 g) of the packing material.

The monomer having a cation exchange group, as used herein, refers to a monomer which has at least one cation exchange group and at least one polymerizable group. The cation exchange group is a functional group that shows the ability to exchange cations in a specific pH range-and can be illustrated by known cation exchange groups, example of which include carboxyl, sulfonic, phosphoric and the like. The polymerizable group is not particularly specified in type and can be illustrated by known polymerizable groups such as vinyl groups.

Examples of monomers having a carboxyl group, as an illustrative cation exchange group, include (meth)acrylic acid, 2-(meth)acryloyloxyethylsuccinic acid, crotonic acid, itaconic acid, citraconic acid, mesaconic acid, maleic acid, fumaric acid, derivatives thereof and the like.

Examples of monomers having a phosphoric group, as an illustrative cation exchange group, include ((meth) acryloyloxyethyl)acid phosphate, (2-(meth) acryloyloxyethyl)acid phosphate, (3-(meth) acryloyloxypropyl)acid phosphate, derivatives thereof and the like.

Examples of monomers having a sulfonic group, as an illustrative cation exchange group, include (meth)allylsulfonic acid, 2-(meth)acrylamide-2-methylpropanesulfonic acid, (3-sulfopropyl)itaconic acid, 3-sulfopropyl(meth) acrylic acid, derivatives thereof and the like.

Besides the above-listed monomers having various cation exchange groups, their derivatives, salts thereof as with sodium or potassium, chlorides thereof and the like may also be useful.

In the present invention, the monomer having a cation exchange group may be in the form of a monomer having a functional group which can be converted to a cation exchange group by a chemical reaction. The functional group on such a monomer may be converted to a cation exchange group by a chemical reaction after the monomer has been polymerized. Illustrative chemical reactions are hydrolysis and a transfer reaction. An illustrative functional group which can be converted to a cation exchange group by a chemical reaction is an ester group. The following specific example can be utilized. A methyl methacrylate monomer is allowed to polymerize and then heated in an alkaline condition so that ester bonds are decomposed to produce the exchange for carboxyl groups, resulting in the preparation of packing materials for cation exchange LC, which comprise a polymeric material as if derived from a monomer having a cation exchange group and a crosslinking monomer.

The amount of the monomer having a cation exchange group may be varied depending upon the particular type of the monomer used, but may preferably be in the range of 10–200 parts by weight, based on 100 parts by weight of the crosslinking monomer. If the amount is less than 10 parts by weight, its cation exchange capacity may become too low to result in a sufficient cation exchange reaction. This lowers the resolution. On the other hand, if the amount exceeds 200 parts by weight, its hydrophilicity may become higher to reduce the resistance to pressure and reswelling. Also, it may require an extended time until the replaced eluent goes to equilibrium. This problematically extends a measurement period. The above-listed monomers may be used in combination, when needed.

The crosslinking monomer used in the present invention may be exemplified by monomers having two or more vinyl groups per molecule, such as below-described (meth)acrylic ester derivatives, aliphatic diene compounds and derivatives thereof. Examples of monomers having two or more vinyl groups per molecule include styrenic derivatives, such as divinylbenzene, divinyltoluene, divinylxylene, divinylethylbenzene and divinylnaphthalene.

Examples of (meth)acrylic ester derivatives include ethylene glycol di(meth)acrylate, polyethylene glycol di(meth)acrylate, 1,3-butylene glycol di(meth)acrylate, 1,6-hexaglycol di(meth)acrylate, neopentyl glycol di(meth)acrylate, polypropylene glycol di(meth)acrylate, trimethylolethane tri(meth)acrylate, trimethylolpropane tri(meth)acrylate, tetramethylolpropane tri(meth)acrylate, tetramethylolmethane tri(meth)acrylate, tetramethylolmethane tetra(meth)acrylate, 2-hydroxy-1,3-di(meth)acryloxypropane, 2-hydroxy-1-acryloxy-3-methacryloxypropane, 1,10-di(meth)acryloxy-4,7-dioxadecane-2,9-diol, 1,10-di(meth)acryloxy-5-methyl-4,7-dioxadecane-2,9-diol, 1,11-di(meth)acryloxy-4,8-dioxadecane-2,6,10-triol, derivatives thereof and the like.

Examples of aliphatic diene compounds include 1,3-butadiene, isoprene, 1,4-hexadiene, derivatives thereof and the like.

The packing material of the present invention can be prepared from the aforementioned monomers by using known polymerization techniques such as suspension polymerization, emulsion polymerization and dispersion polymerization. Japanese Patent Publication No. Hei 8-7197 describes a particularly preferred technique which comprises, in sequence, preparing crosslinking polymer particles from a crosslinking monomer, impregnating a polymerization initiator into the polymer particles, adding a monomer having an ion exchange group, and polymerizing the mixture.

In the present invention, the polymerization initiator used in the polymerization of monomers is not particularly specified in type and may be a known water- or oil-soluble free-radical polymerization initiator. Examples of free-radical initiators include persulfates such as potassium persulfate, sodium persulfate and ammonium persulfate; organic peroxides such as cumene hydroperoxide, benzoyl peroxide, lauroyl peroxide, octanoyl peroxide, o-chlorobenzoyl peroxide, acetyl peroxide, t-butyl hydroperoxide, t-butyl peroxyacetate, t-butyl peroxyisobutylate, 3,5,5-trimethylhexanoyl peroxide, t-butylperoxy-2-ethylhexanoate and di-t-butyl peroxide; and azo compounds such as 2,2-azobisisobutyronitrile, 2,2-azobis(2,4-dimethylvaleronitrile), 4,4-azobis(4-cyanopentanoic acid), 2,2-azobis(2-methylbutyronitrile), 2,2-azobis(2,4-dimethylvaleronitrile) and azobiscyclohexanecarbonitrile.

Preferably, the amount of the polymerization initiator is maintained in the range of 0.05–1 part by weight, based on 100 parts by weight of the crosslinking monomer. If the initiator amount is less than 0.05 parts by weight, the resulting polymerization may become insufficient or require an extended period of time. On the other hand, if the amount exceeds 1 part by weight, the reaction may be caused to proceed rapidly and possibly produce aggregates. The polymerization initiator is preferably used in the form of being dissolved in the crosslinking monomer.

In addition to the crosslinking monomer and others as described above, other additives such as a non-crosslinking monomer, an organic solvent and polymer particles may also be loaded in the preparation of the aforementioned polymer. Such additives are known in the art and are not limited to those illustrated below.

Examples of non-crosslinking monomers include styrenic derivatives such as styrene, α-methylstyrene, p-methylstyrene and chloromethylstyrene; aliphatic monomers such as vinyl chloride; vinyl esters such as vinyl acetate, vinyl propionate and vinyl stearate; and acrylic acid derivatives such as methyl (meth)acrylate, ethyl (meth)acrylate, butyl (meth)acrylate, 2-ethylhexyl (meth)acrylate, stearyl (meth)acrylate, (meth)acrylamide, (meth)acrylonitrile and glycidyl (meth)acrylate.

The amount of the non-crosslinking monomer may be varied depending upon the particular type of the monomer used, but may preferably be in the range of 0–100 parts by weight, based on 100 parts by weight of the crosslinking monomer. The above-listed non-crosslinking monomers may be used in combination, when needed.

The type of the organic solvent may be selected from those known in the art depending upon the types of the monomers used. Examples of organic solvents include aromatic hydrocarbons such as toluene, xylene, diethylbenzene and dodecylbenzene; saturated hydrocarbons such as hexane, heptane, octane and decane; alcohols such as methanol, ethanol, isopropyl alcohol, butyl alcohol, isoamyl alcohol, hexyl alcohol and octyl alcohol; amines such as dimethylformamide; and ethers such as diethyl ether.

These organic solvents may be added in the form of incorporating the crosslinking monomer or cation exchange group-containing monomer dissolved therein, or separately added to a dispersing medium. They may be added either initially or during the polymerization preferably in the amount of 0–300 parts by weight, based on 100 parts by weight of the crosslinking monomer.

The aforementioned polymer particles have a uniform particle size distribution. When they are added to either the crosslinking monomer or a mixture thereof with the cation exchange group-containing monomer, the subsequent polymerization allows production of packing materials having a uniform particle size distribution. Examples of polymer particles include particles of non-crosslinking polymer made via homo- or co-polymerization of the above-listed non-crosslinking monomers, such as a styrene polymer, styrene-divinylbenzene copolymer, methyl (meth)acrylate polymer and ethyl (meth) acrylate polymer. Also useful for the polymer particles are crosslinked copolymer particles derived from the aforementioned non-crosslinking monomer and crosslinking monomer. In such a case, low-crosslinking-polymer particles containing up to 10% crosslinking polymer may preferably be used.

The polymer particles can be produced by polymerization techniques known in the art, e.g., made via emulsion, soap-free, dispersion or suspension polymerization.

Preferably, the polymer particles have a mean particle diameter of 0.1–10 μm with a coefficient of variation (CV value (%))=15% or below (CV value (%)=(standard deviation/mean particle diameter)×100).

The amount of polymer particles may preferably be in the range of 0.5–100 parts by weight, based on 100 parts by weight of the crosslinking monomer.

The packing material of the present invention has pores with an average diameter of 10–100 angstroms. Outside this range, the following problems arise. It is generally difficult to produce packing materials having pores with an average diameter of below 10 angstroms in a controlled and reproducible fashion. Packing materials having pores with an average diameter of exceeding 100 angstroms readily swell and shrink to possibly cause variations in pressure loss during measurement. Also in the case where plural eluents are used, it requires a long time before an intrerior of a column goes to equilibrium whenever the eluent is changed.

The specific surface area of the packing material of the present invention is in the 0.05–5 m² per unit dry weight (1 g) of the packing material. Outside this range, the following problems arise. If the specific surface area falls below 0.05 m²/g, the particle diameter of the packing material becomes large to result in the reduced resolutions. If it exceeds 5 m²/g, the particle diameter of the packing material becomes very small to result in the increased pressure loss.

The pore volume of the packing material of the present invention is in the range of 0.1–10 μL per unit dry weight (1 g) of packing material. Outside this range, the following problems arise. It is generally difficult to produce packing materials having a pore volume of below 0.1 μL/g in a controlled and reproducible fashion. Packing materials having pore volumes of exceeding 10 μL/g readily swell and shrink to possibly cause variations in pressure loss during measurement. Also in the case where plural eluents are used, it requires a long time before an intrerior of a column goes to equilibrium whenever the eluent is changed.

The ion exchange capacity of the packing material of the present invention is in the range of 1–100 μeq per unit dry weight (1 g) of packing material. Outside this range, the following problems arise. If the exchange capacity is below 1 μeq/g, an exchange reaction associated with a sample to be measured becomes difficult to occur to result in the reduced resolutions. If the exchange capacity exceeds 100 μeq/g, it requires a long time before an intrerior of a column goes to equilibrium, resulting in the prolonged measurement time and reduced pressure resistance.

In the present invention, the mean pore diameter, specific surface area, pore volume and ion exchange capacity, must fall within the above-specified ranges, respectively. These are essential features of the present invention. It becomes hard to obtain advantageous effects of the present invention unless each and every one of the above-listed physical properties falls within the specified range.

Preferably, the packing material of the present invention has a mean particle diameter of 1–20 μm with a preferred CV value (%)=40% or below. If necessary, it may be subjected to a known dry or wet classification process to adjust their mean particle diameter and CV value within the above-specified ranges.

The packing material of the present invention is used generally in the form of being packed in a stainless steel column. The technique used to pack the column with the packing material is not particularly specified. However, the use of a wet process (slurry process) is particularly preferred. In the wet process, the packing material is packed in the column by allowing them to disperse in an eluting medium and then pass under pressure through a packer and other devices into a column.

In the present invention, an LC filter is preferably used comprising at least one-inert material selected from polyether ketones and polyethylens.

The inert material, as used herein, refers to an inert material conventionally known as being useful for analysis of biosamples. The use of this inert material reduces the occurrence of clogging during a long-term filter service.

The LC filter comprising the above-referred inert material has been devised on the basis of the following findings. That is, the use of the conventional stainless steel filter in the determination of hemoglobins according to the present invention resulted in the increased tendency of hemoglobins and other components present in a blood specimen to become adsorbed to the filter, which caused the poor separation thereof and the increased occurrence of clogging. It has been discovered that such problems can be solved by substituting the filter material for the above-described inert material.

Notwithstanding the above, if there is a possibility that the components present in the sample may adsorb to the filter in a manner to affect measurements, a blocking agent may preferably be used to block the filter and/or column. Specific examples of such blocking agents include proteins such as bovine serum albumin, casein, gelatin, hemoglobin and myoglobin; polar lipids such as phospholids; surfactants such as sodium dodecyl sulfate and polyethylene glycol mono-4-octylphenyl ether (Triton X-100); and the like.

The polyether ketones as described above are refractory crystalline polymers having a combined structure of phenyl ketone and phenyl ether, examples of which include polyether ether ketone (generally called PEEK resin) represented by the following chemical formula (1); polyallyl ether ketone; polyether ketone ketone; polyether kotone ether ketone ketone; and the like. Particularly preferred is polyether ether ketone.

[Chemical formula I]

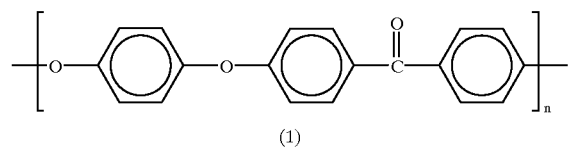

(1)

The LC filter of the present invention may be comprised of material containing at least one of polyether ketone and polyethylene. Examples of such materials include a single substance of polyether ketone or polyethylene; a mixture of polyether ketone and fluoro resin, a mixture of polyethylene and fluoro resin; and the like.

The filter of the present invention can be constructed in any configuration, so long as it does not cause a turbulent fluid flow. For example, it may be constructed in various configurations, as shown in FIG. 26, including (a) a cylinder, (b) cone, (c) truncated cone, (d) combination of cylinder and cone, (e) combination of truncated cone and cylinder and (f) combination of two cones.

The filter of the present invention is sized to have a diameter preferably of 1–100 mm and more preferably of 2–50 mm, and a thickness preferably of 0.1–10 mm and more preferably of 0.5–5 mm. The filter has pores with a mean diameter generally known in the art, preferably in the range of 0.1–20 μm, more preferably in the range of 0.2–10 μm.

The filter of the present invention may be used for a line filter for LC, or for a filter at a column inlet or outlet.

FIG. 27 is a sectional view of a line filter 15 which is constructed in a configuration whereby the filter 11 of the present invention is fitted in a holder 13. In this line filter 15, the filter 11 of the present invention is accommodated within the holder 13.

If necessary, a seal member 12 may be provided to maintain an air-tight seal between the holder 13 and the filter 11. Specifically, the seal member 12 may be disposed circumferentially of the filter 11 to make an air-tight joint between the holder 13 and the filter 11, as shown in FIGS. 28(a) and 28(b).

The material type of seal member is not particularly specified, so long as it has a sufficient strength to hold the filter. Examples of material types include polyether ketones, a fluoro resin, a mixture of polyether ether ketone and a fluoro resin and stainless steel. Preferably, the seal member is sized and configured so that it conforms to a shape of the filter and restricts diffusion of a sample.

The LC column of the present invention is characterized as incorporating the LC filter of the present invention.

The LC column of the present invention will be now described.

The LC column of the present invention uses the filter of the present invention for its inlet filter and an outlet filter.

As shown in FIG. 29, the LC column of the present invention is similar in construction to LC columns conventionally known in the art, excepting the use of the filter of the present invention for the filter 11. In FIG. 29, reference numeral 40 indicate a separation column main body and reference numeral 42 indicates an end fitting.

The hemolyzing reagent for use in the present invention is a hemolyzing reagent which can be utilized to hemolyze a blood specimen in the method for determining hemoglobins in accordance with the present invention. Preferably, the hymolyzing reagent contains a chaotropic ion which is effective to further improve the separation of stable $HbA_{1c}$. The details of the chaotropic ion used are similar to those described in the first invention.

More preferably, the hemolyzing reagent also contains a buffering agent which shows an buffer action in the 5.0–10.0 pH range. The pH of the hemolyzing reagent used in the present invention is in the range of 5.0–10.0, preferably in the range of 5.5–9.5, more preferably in the range of 6.0–9.0. If the pH is lower than 5.0 or higher than 10.0, modification of hemoglobins is caused to occur.

The LC equipment for use in the present invention may have a construction known in the art, such as including a liquid delivery pump, a sample injecting device (sampler), a column and a detector. Other supplemental devices (such as a constant-temperature bath for the column and a deairing device for an eluent) may further be incorporated when needed.

Other conditions applicable to the above-described determination method are generally known in the art. The flow rate of the eluent is preferably 0.05–5 mL/min, more preferably 0.2–3 mL/min. While not limiting, a 415 nm visual light may preferably be used to detect hemoglobins. A sample subject to measurement is generally prepared by diluting a hemolyzed liquid derived via hemolysis with a solution containing material capable of activating hemolysis, such as a surfactant. The amount of the sample injected is varied depending upon the dilution ratio of the blood specimen, and may preferably in the approximate range of 0.1–100 $\mu$L.

BEST MODE FOR CARRYING OUT THE INVENTION

Figure 1:
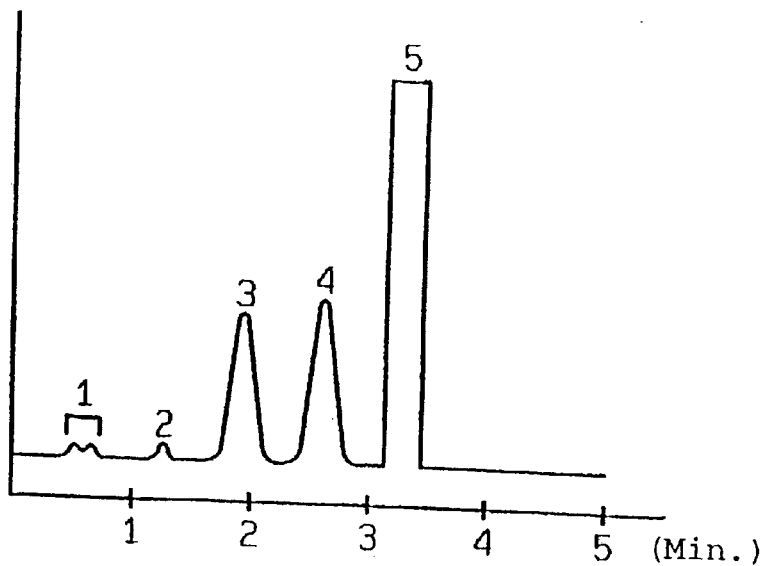
FIG. 1 is a chromatogram obtained when determination of hemoglobins (sample a) was performed under the conditions of Example 1.

The present invention is below described in detail with reference to non-limiting Examples and Comparative Examples.

EXAMPLE 1

Preparation of Packing Material 1.5 g of benzoyl peroxide (product of Wako Co., Ltd.) was allowed to disolve in a mixture containing 400 g of tetraethylene glycol dimethacrylate (product of Shin-Nakamura Chem. Co., Ltd.) and 150 g of 2-acrylamide-2-methylpropanesulfonic acid. The resulting mixture was dispersed in 2500 mL of a 4 wt. % aqueous solution of polyvinyl alcohol (product of Nippon Gosei Chem. Co., Ltd.), heated with agitation under a nitrogen atmosphere to 75° C. and then allowed to polymerize for 8 hours. Thereafter, the polymers were washed, dried and classified to obtain particles with a mean particle diameter of 6 $\mu$m.

Packing of the Material into a Column

The particles obtained were packed into a column according to the following procedure.

0.7 g of the above-obtained particles was dispersed in 30 mL of a 50 mM phosphate buffer (pH 5.8), subjected to an ultrasonic treatment for 5 minutes and stirred well. The whole content was introduced into a packer (product of Umetani Seiki Co., Ltd.) connected to a vacant stainless steel column (inner diameter 4.6×30 mm). The content was packed under a constant pressure of 300 kg/cm$^2$ into the column by a delivery pump (product of Sanuki Ind. Co., Ltd.) connected thereto.

Measurement of Hemoglobins

Using the packed column, hemoglobins were measured under the following conditions.

(Measurement Conditions)
System:
  delivery pump: LC-9A (manufactured by Shimadzu Co., Ltd.)
  autosampler: ASU-420 (manufactured by Sekisui Chem. Co., Ltd.)
  detector: SPD-6AV (manufactured by Shimadzu Co., Ltd.)
Eluents:
  eluent A: 50 mM phosphate buffer (pH 5.3) containing 50 mM perchloric acid
  eluent B: 50 mM phosphate buffer (pH 8.0) containing 200 mM perchloric acid The pKa values of phosphate are indicated in Table 1. The elunt A was delivered for the initial 3-minute period, the eluent B for the subsequent 0.2-minute period and again the eluent A for the final 1.8-minute period.

Flow rate: 2.0 mL/min
Detection wavelength: 415 nm
Sample injection: 10 $\mu$L (Measurement Samples)

The following samples were prepared from a whole blood specimen collected with sodium fluoride from a healthy human. A phosphate buffer solution (pH 7.0) containing 0.1 wt. % polyethylene glycol mono-4-octylphenyl ether (Triton X-100) (product of Tokyo Chemical Industry, Ltd.) was used as a hemolyzing reagent.

a) Glucose-added sample: 500 mg/dL of an aqueous glucose solution was added to the whole blood specimen and allowed to react at 37° C. for 3 hours. The resultant was then subjected to hemolysis by the aforementioned hemolyzing reagent, followed by 150-fold dilution. As a result, a sample a was obtained.

b) CHb-containing sample: 1 mL of 0.3 wt. % sodium cyanate solution in saline was added to 10 mL of the whole blood specimen and allowed to react at 37° C. for 3 hours. The resultant was subsequently subjected to hemolysis by the aforementioned hemolyzing reagent, followed by 150-fold dilution. As a result, a sample b was obtained.

c) AHb-containing sample: 1 mL of 0.3 wt. % acetaldehyde solution in saline was added to 10 mL of the whole blood specimen and allowed to react at 37° C. for 3 hours. The resultant was subsequently subjected to hemolysis by the aforementioned hemolyzing reagent, followed by 150-fold dilution. As a result, a sample c was obtained.

(Measurement Results)

Figure 2:
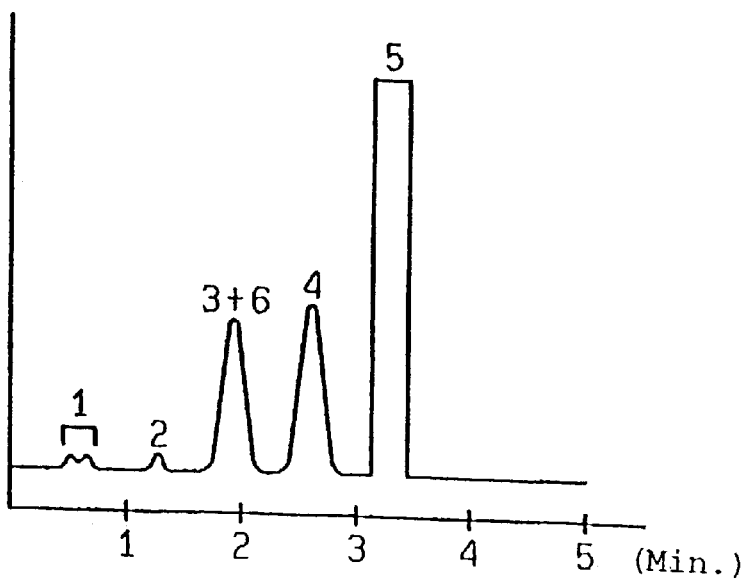
FIG. 2 is a chromatogram obtained when determination of hemoglobins (sample b) was performed under the conditions of Example 1.
Figure 3:
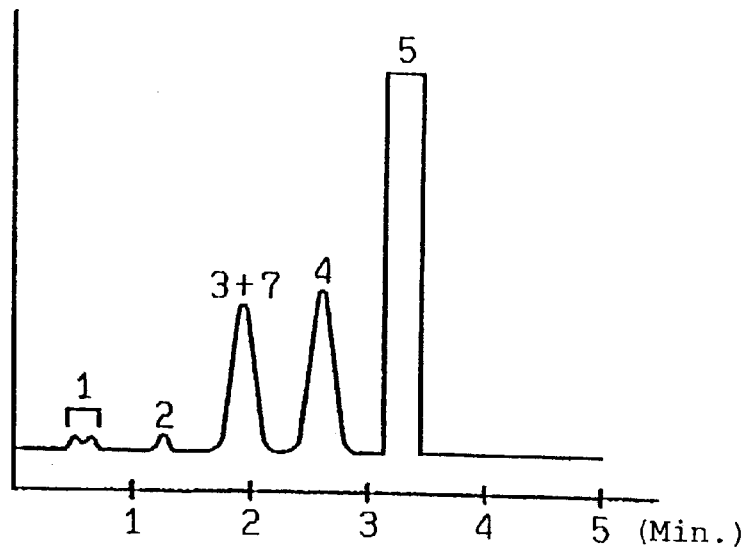
FIG. 3 is a chromatogram obtained when determination of hemoglobins (sample c) was performed under the conditions of Example 1.

The chromatograms obtained when measurement of the sample was performed under the above-specified conditions are shown in FIGS. 1–3. FIGS. 1–3 show the results measured for the samples, a, b and c. Peak 1 represents HbA$_{1a}$ and HbA$_{1b}$. Peak 2 represents HbF. Peak 3 represents labile HbA$_{1c}$. Peak 4 represents stable HbA$_{1c}$. Peak 5 represents HbA$_0$. Peak 6 represents CHb and Peak 7 represents AHb.

In FIG. 1, Peaks 3 and 4 are well separated from each other. Peak 6 (CHb) is well separated from Peak 4 in FIG. 2. Peak 7 (AHb) is well separated from Peak 4 in FIG. 3.

EXAMPLE 2

Measurement of hemoglobins was performed in the same manner as in Example 1, with the exception that the eluents were changed in composition to the followings. Satisfactory chromatograms were obtained as similar to those shown in FIGS. 1–3.

Eluents:
  eluent A: 20 mM succinate-20 mM phosphate buffer (pH 5.3) containing 55 mM perchloric acid
  eluent B: 20 mM succinate-20 mM phosphate buffer (pH 8.0) containing 250 mM perchloric acid The pKa values of succinate are indicated in Table 1.

EXAMPLE 3

Measurement of hemoglobins was performed in the same manner as in Example 1, with the exception that the eluents were changed in composition to the followings. Satisfactory chromatograms were obtained as similar to those shown in FIGS. 1–3.

Eluents:
- eluent A: 10 mM maleate-40 mM phosphate buffer (pH 5.3) containing 55 mM sodium nitrate
- eluent B: 10 mM maleate-40 mM phosphate buffer (pH 8.3) containing 200 mM sodium nitrate The pKa values of maleate are given in Table 1.

EXAMPLE 4

Measurement of hemoglobins was performed in the same manner as in Example 1, with the exception that the eluents were changed in composition to the followings. Satisfactory chromatograms were obtained as similar to those shown in FIGS. 1–3.

Eluents:
- eluent A: 10 mM maleate-50 mM phosphate buffer (pH 5.3) containing 50 mM perchloric acid
- eluent B: 8 mM maleate-50 mM phosphate buffer (pH 8.3) containing 200 mM perchloric acid

Comparative Example 1

Measurement of hemoglobins was performed in the same manner as in Example 1, with the exception that the eluents were changed in composition to the followings.

Eluents:
- eluent A: 100 mM succinate buffer (pH 5.4)
- eluent B: 300 mM succinate buffer (pH 8.0)

Figure 4:
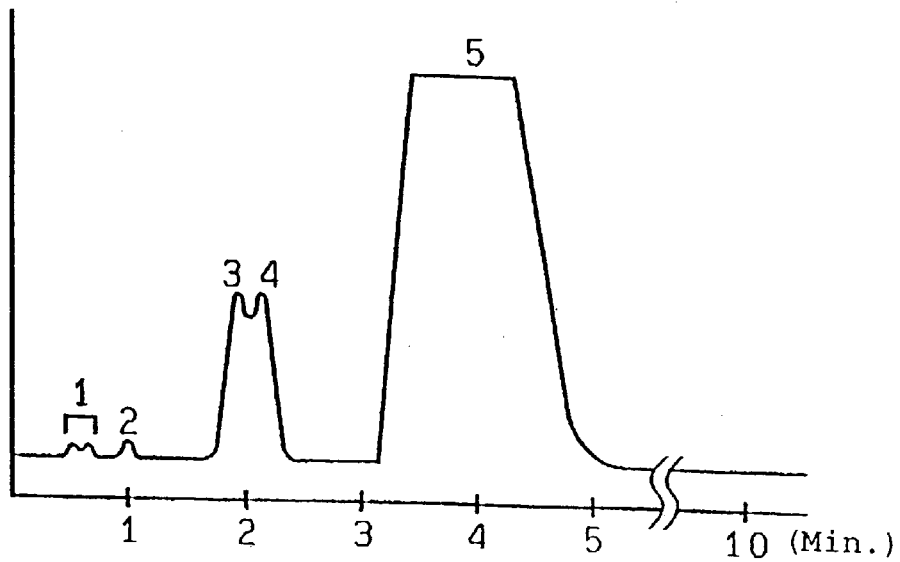
FIG. 4 is a chromatogram obtained when determination of hemoglobins (sample a) was performed under the conditions of Comparative Example 1.
Figure 5:
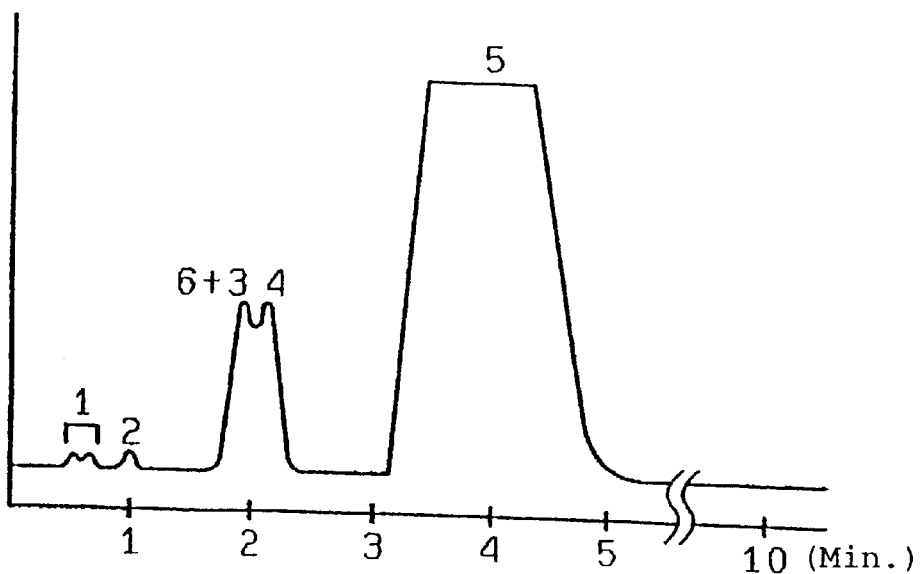
FIG. 5 is a chromatogram obtained when determination of hemoglobins (sample b) was performed under the conditions of Comparative Example 1.
Figure 6:
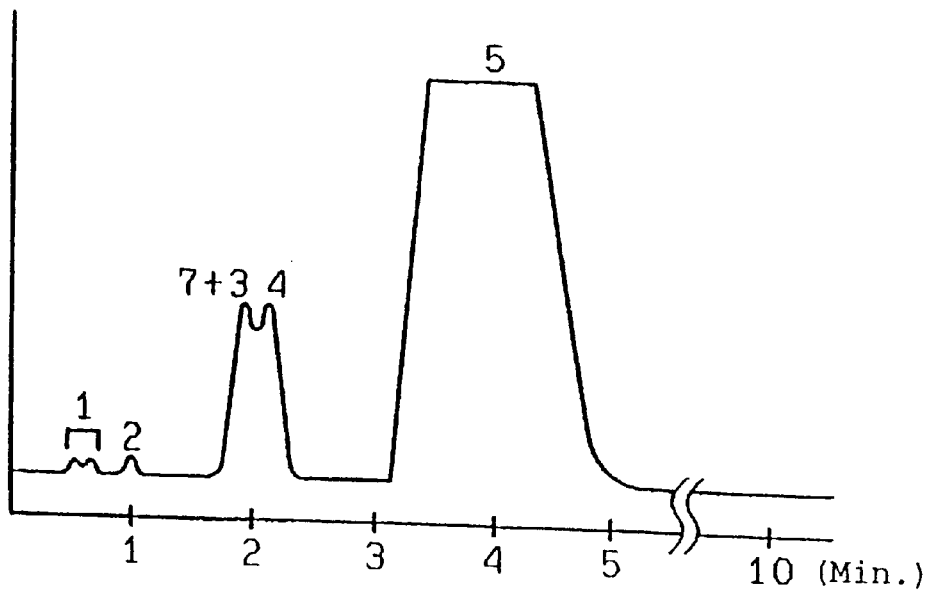
FIG. 6 is a chromatogram obtained when determination of hemoglobins (sample c) was performed under the conditions of Comparative Example 1.

The chromatograms obtained are shown in FIGS. 4–6. FIGS. 4–6 show the measurement results for the samples a, b and c, respectively. Notwithstanding the extended measurement time, such chromatograms reveal the poorer separation compared to those shown in FIG. 1–3.

Comparative Example 2

Measurement of hemoglobins was performed in the same manner as in Example 1, with the exception that the eluents were changed in composition to the followings. The obtained chromatograms were similar to those shown in FIGS. 4–6.

Eluents:
- eluent A: 200 mM phosphate buffer (pH 5.4)
- eluent B: 330 mM phosphate buffer (pH 6.0)

EXAMPLE 5

Measurement of hemoglobins was performed in the same manner as in Example 1, with the exception that the eluents were changed in composition to the followings.

Eluents:
- eluent A: 50 mM phosphate buffer (pH 5.3) containing 55 mM perchloric acid
- eluent B: 50 mM phosphate buffer (pH 8.0) containing 200 mM perchloric acid During the measurement, the eluent A was delivered for the initial 3-minute period, the eluent B for the subsequent 0.2-minute period and again the eluent A for the final 1.8-minute period.

(Measurement Results)

Figure 7:
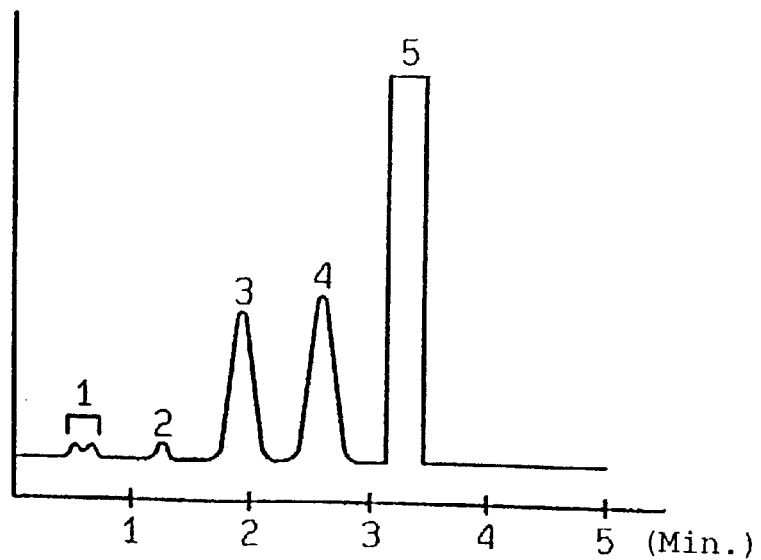
FIG. 7 is a chromatogram obtained when determination of hemoglobins (sample a) was performed under the conditions of Example 5.
Figure 8:
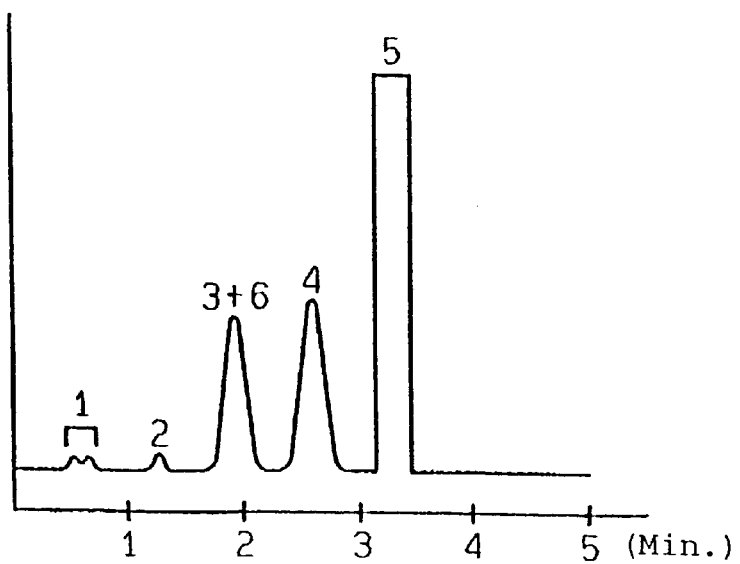
FIG. 8 is a chromatogram obtained when determination of hemoglobins (sample b) was performed under the conditions of Example 5.
Figure 9:
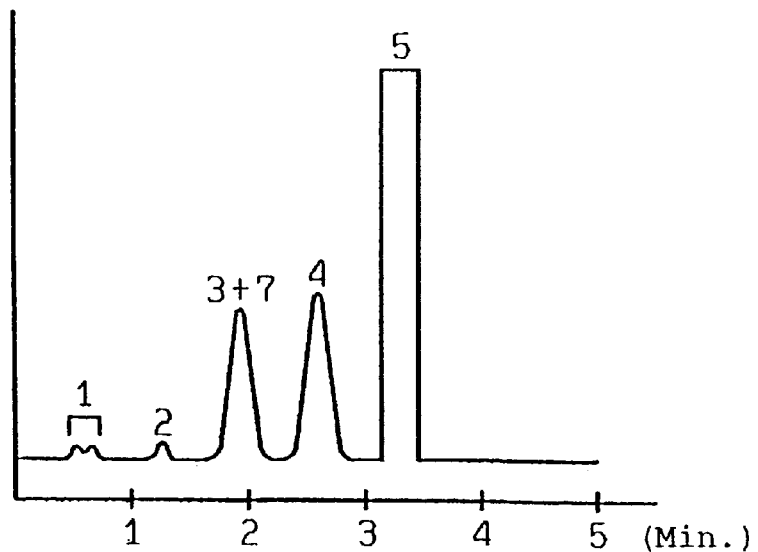
FIG. 9 is a chromatogram obtained when determination of hemoglobins (sample c) was performed under the conditions of Example 5.

The chromatograms obtained are shown in FIGS. 7–9. FIGS. 7–9 show the results measured for the samples a, b and c, respectively. Peak 1 represents $HbA_{1a}$ and $HbA_{1b}$. Peak 2 represents HbF. Peak 3 represents labile $HbA_{1c}$. Peak 4 represents stable $HbA_{1c}$. Peak 5 represents $HbA_0$. Peak 6 represents CHb and Peak 7 represents AHb.

In FIG. 7, Peaks 3 and 4 are well separated from each other. Peak 6 (CHb) is well separated from Peak 4 in FIG. 8. Peak 7 (AHb) is well separated from Peak 4 in FIG. 9.

EXAMPLE 6

Measurement of hemoglobins was performed in the same manner as in Example 1, with the exception that the eluents were changed in composition to the followings. Satisfactory chromatograms were obtained as similar to those shown in FIGS. 7–9.

Eluents:
- eluent A: 25 mM succinate-20 mM phosphate buffer (pH 5.3) containing 48 mM sodium nitrate
- eluent B: 25 mM succinate-20 mM phosphate buffer (pH 8.0) containing 200 mM sodium nitrate

EXAMPLE 7

Measurement of hemoglobins was performed in the same manner as in Example 1, with the exception that the eluents were changed in composition to the followings. Satisfactory chromatograms were obtained as similar to those shown in FIGS. 7–9.

Eluents:
- eluent A: 25 mM succinate-20 mM phosphate buffer (pH 5.3) containing 53 mM perchloric acid
- eluent B: 25 mM succinate-20 mM phosphate buffer (pH 8.0) containing 200 mM perchloric acid

EXAMPLE 8

Measurement of hemoglobins was performed in the same manner as in Example 1, with the exception that the eluents were changed in composition to the followings. Satisfactory chromatograms were obtained as similar to those shown in FIGS. 7–9.

Eluents:
- eluent A: 25 mM succinate buffer (pH 5.3) containing 48 mM sodium nitrate
- eluent B: 30 mM phosphate buffer (pH 8.3) containing 200 mM sodium nitrate

Comparative Example 3

Measurement of hemoglobins was performed in the same manner as in Example 1, with the exception that the eluents were changed in composition to the followings.

Eluents:
- eluent A: 170 mM phosphate buffer (pH 5.3)
- eluent B: 330 mM phosphate buffer (pH 5.7)

Figure 10:
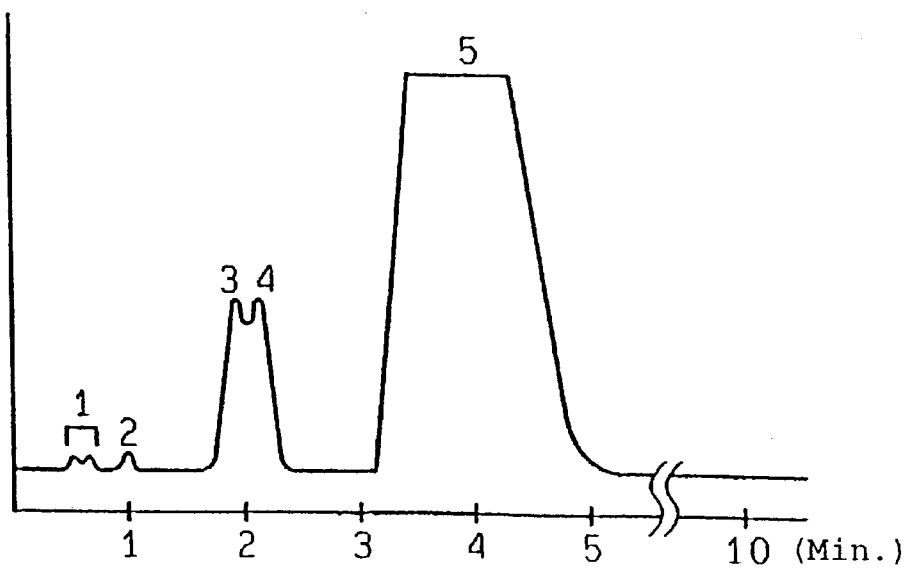
FIG. 10 is a chromatogram obtained when determination of hemoglobins (sample a) was performed under the conditions of Comparative Example 3.
Figure 11:
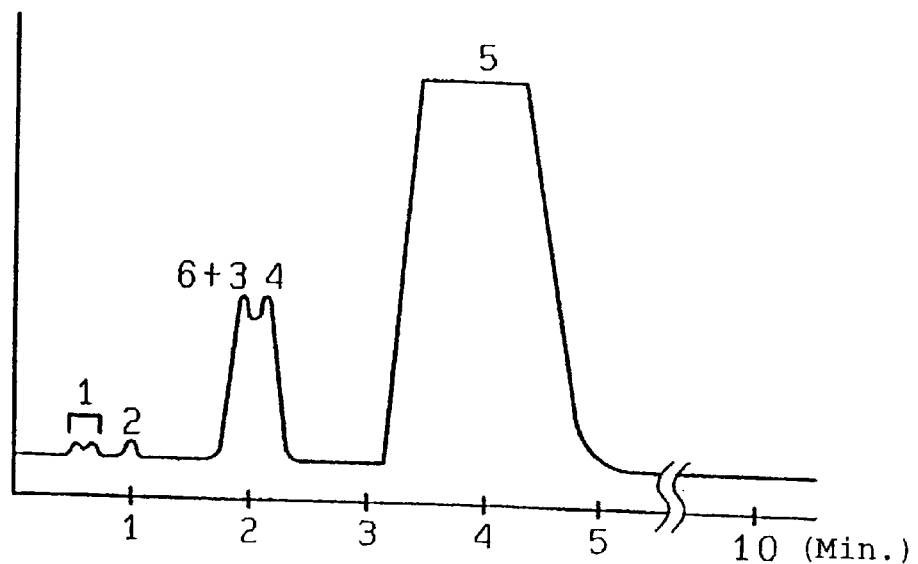
FIG. 11 is a chromatogram obtained when determination of hemoglobins (sample b) was performed under the conditions of Comparative Example 3.
Figure 12:
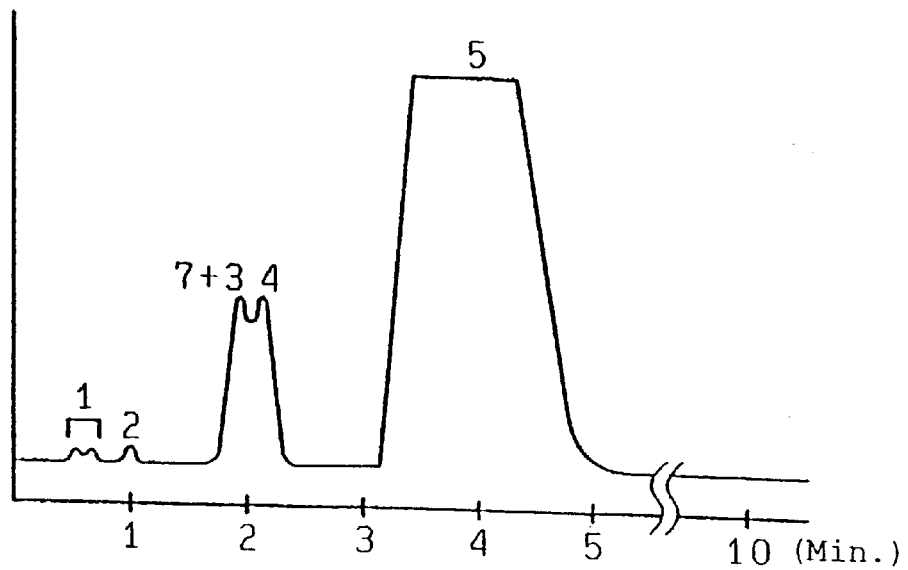
FIG. 12 is a chromatogram obtained when determination of hemoglobins (sample c) was performed under the conditions of Comparative Example 3.

The chromatograms obtained are shown in FIGS. 10–12. FIGS. 10–12 show the results measured for the samples a, b and c, respectively. Notwithstanding the extended measurement time, such chromatograms reveal poorer separation compared to those shown in FIG. 7–9.

Comparative Example 4

Measurement of hemoglobins was performed in the same manner as in Example 1, with the exception that the eluents were changed in composition to the followings. The obtained chromatograms were similar to those shown in FIGS. 10–12.

Eluents:
- eluent A: 100 mM succinate buffer (pH 5.6)
- eluent B: 250 mM succinate buffer (pH 6.5)

The chromatograms obtained in Examples 5–8 reveal the reduced $HbA_0$ peak widths and increased resolutions when compared to those obtained in Comparative Examples 3 and 4.

EXAMPLE 9

Measurement of hemoglobins was performed in the same manner as in Example 1, with the exception that the number of eluents, their compositions and delivery condition were altered to the followings.

Eluents:
  eluent A: 50 mM phosphate buffer (pH 5.3) containing 55 mM perchloric acid
  eluent B: 50 mM phosphate buffer (pH 5.3) containing 68 mM perchloric acid
  eluent C: 50 mM phosphate buffer (pH 8.0) containing 200 mM perchloric acid During the measurement, the eluent A was delivered for the initial 0.7-minute period, the eluent B for the next 0.7-minute period, the eluent C for the next 0.1-minute period and again the eluent A for the final 0.4-minute period.

(Measurement Results)

Figure 13:
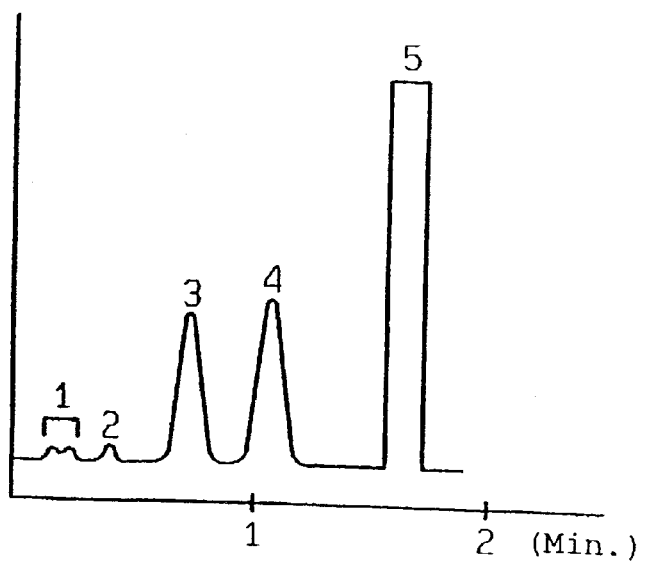
FIG. 13 is a chromatogram obtained when determination of hemoglobins (sample a) was performed under the conditions of Example 9.
Figure 14:
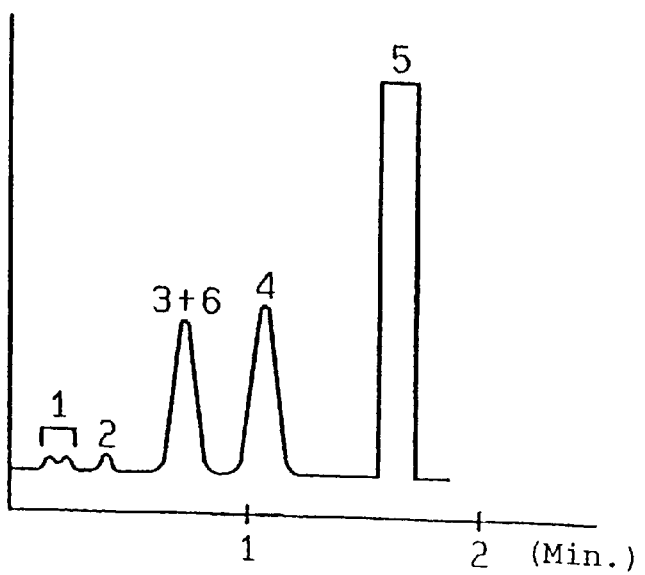
FIG. 14 is a chromatogram obtained when determination of hemoglobins (sample b) was performed under the conditions of Example 9.
Figure 15:
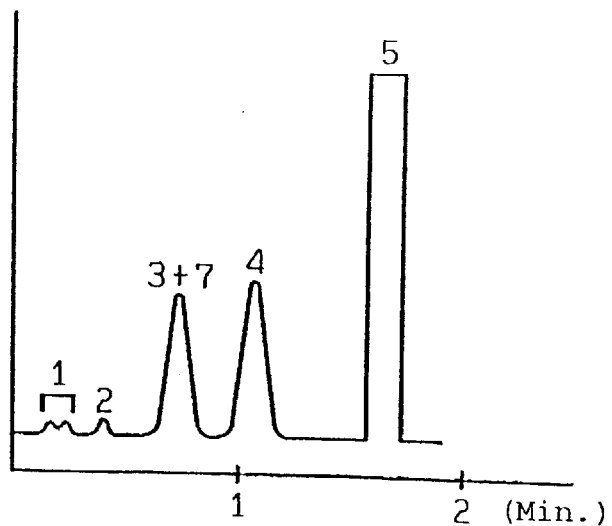
FIG. 15 is a chromatogram obtained when determination of hemoglobins (sample c) was performed under the conditions of Example 9.

The chromatograms obtained are shown in FIGS. 13–15. FIGS. 13–15 show the results measured for the samples, a, b and c, respectively. Peak 1 represents $HbA_{1a}$ and $HbA_{1b}$. Peak 2 represents HbF. Peak 3 represents labile $HbA_{1c}$. Peak 4 represents stable $HbA_{1c}$. Peak 5 represents $HbA_0$. Peak 6 represents CHb and Peak 7 represents AHb.

In FIG. 13, Peaks 3 and 4 are well separated from each other. Peak 6 (CHb) is well separated from Peak 4 in FIG. 14. Peak 7 (AHb) is well separated from Peak 4 in FIG. 15.

EXAMPLE 10

Measurement of hemoglobins was performed in the same manner as in Example 9, with the exception that the eluents were changed in composition to the followings. Satisfactory chromatograms were obtained as similar to those shown in'FIGS. 13–15.

Eluents:
  eluent A: 25 mM succinate-20 mM phosphate buffer (pH 5.3) containing 48 mM perchloric acid
  eluent B: 25 mM succinate-20 mM phosphate buffer (pH 5.3) containing 67 mM perchloric acid
  eluent C: 25 mM succinate-20 mM phosphate buffer (pH 8.0) containing 200 mM perchloric acid

EXAMPLE 11

Measurement of hemoglobins was performed in the same manner as in Example 9, with the exception that the eluents were changed in composition to the followings. Satisfactory chromatograms were obtained as similar to those shown in FIGS. 13–15.

Eluents:
  eluent A: 20 mM maleate-20 mM phosphate buffer (pH 5.3) containing 53 mM perchloric acid
  eluent B: 20 mM maleate-20 mM phosphate buffer (pH 5.3) containing 68 mM perchloric acid
  eluent C: 20 mM maleate-20 mM phosphate buffer (pH 8.5) containing 200 mM perchloric acid

EXAMPLE 12

Measurement of hemoglobins was performed in the same manner as in Example 9, with the exception that the eluents were changed in composition to the followings. Satisfactory chromatograms were obtained as similar to those shown in FIGS. 13–15.

Eluents:
  eluent A: 25 mM succinate buffer (pH 5.3) containing 48 mM sodium nitrate
  eluent B: 25 mM succinate buffer (pH 5.3) containing 71 mM sodium nitrate
  eluent C: 30 mM phosphate buffer (pH 8.3) containing 200 mM sodium nitrate

EXAMPLE 13

Figure 16:
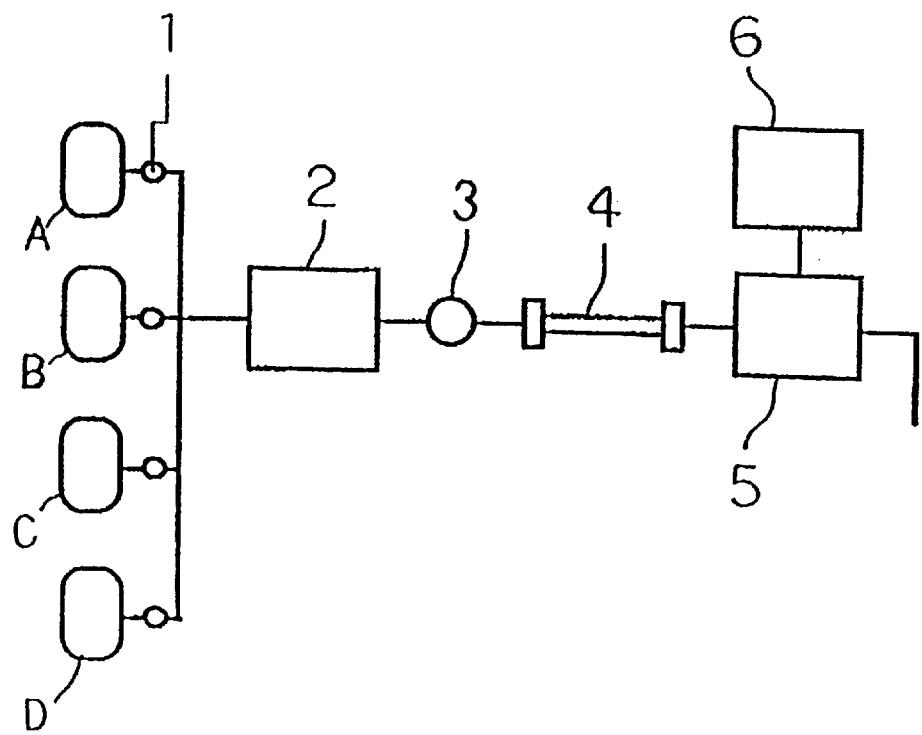
FIG. 16 is a schematic view showing an exemplary construction of an apparatus for use in the stepwise elution process.
Figure 17:
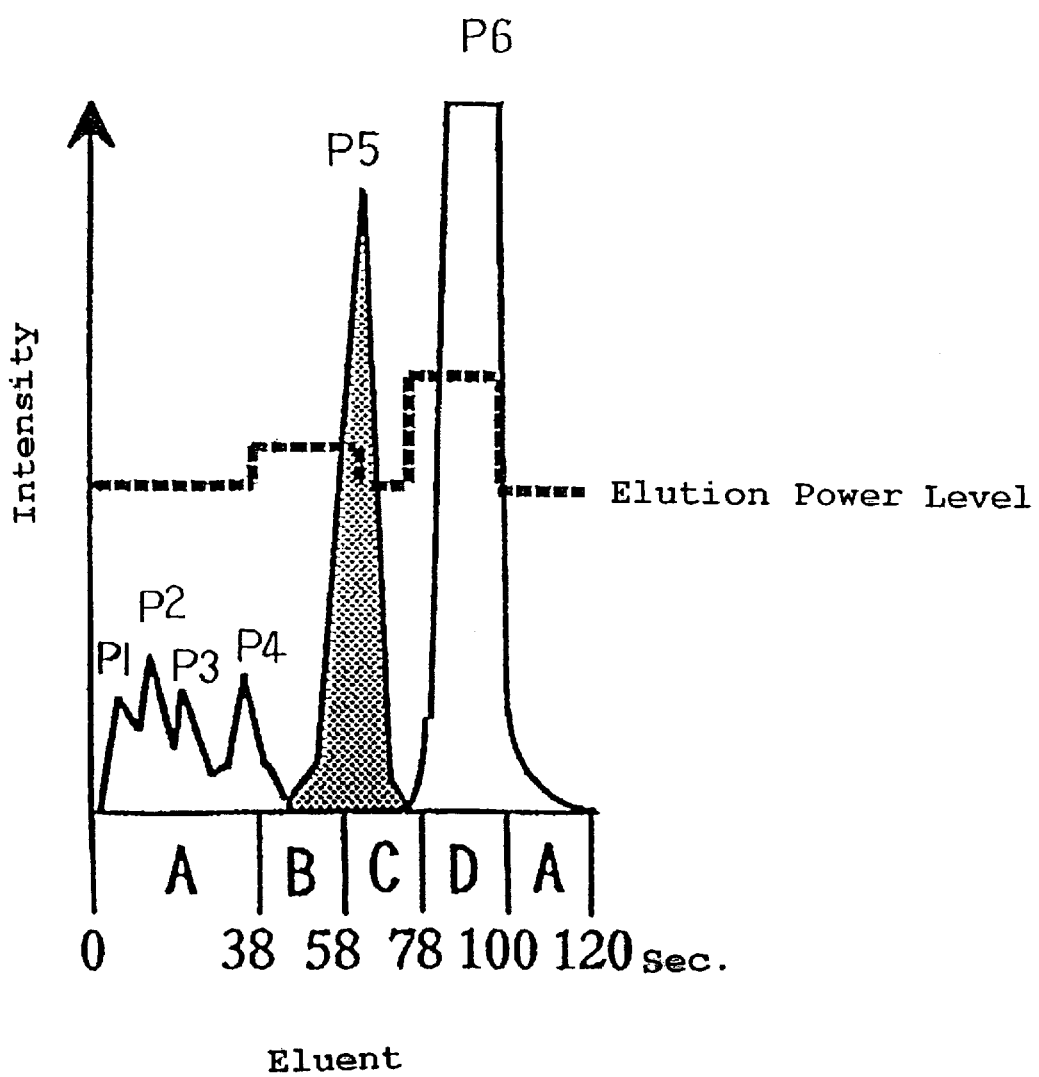
FIG. 17 shows a condition under which the eluents of Example 13 are sequentially passed through a column and a resulting chromatogram.

Measurement of hemoglobins present in a blood sample was carried out using the equipment shown in FIG. 16. A column packed with a cation exchange resin (Micronex $A_{1c}$ HS-IV, product of Sekisui Chem. Co., Ltd.) was used. A 170 mM phosphate buffer, a 190 mM phosphate buffer, a 150 mM phosphate buffer and a 330 mM phosphate buffer, each having a pH of 6, were used as eluents A, B, C and D, respectively. A sample was obtained by subjecting the whole blood used in Example 1 to 100-fold hemolytical dilution with a hemolyzing reagent. The eluents were sequentially delivered according to a stepwise gradient elution technique so that $HbA_{1c}$ (below-described peak P5) was separated from the other hemoglobin peaks within 2 minutes. The elution sequence, as well as a resulting chromatogram, are shown in FIG. 17. That is, the eluent A was delivered for an initial 38-second period, the eluent B having a higher elution power for the next 20-second period, the eluent C having a lower elution power for the next 20-second period, the eluent D having the highest elution power for the next 22-second period and again the eluent A for the final 20-second period. Peak detection was achieved at an absorption intensity of 415 nm.

In the chromatogram shown in FIG. 17, peaks P1–P3 represents $HbA_{1a}$ and $HbA_{1b}$, a peak P4 represents HbF, a peak P5 represents $HbA_{1c}$, and a peak P6 represents $HbA_0$.

During the above-described procedure, the eluent B is changed to the eluent C having a lower elution power. This is done to prevent the earlier elution of the peak, P6, that may be caused by the increase in elution power when the eluent is changed from A to B to interfere with the precise detection of the $HbA_{1c}$, peak, P5.

To evaluate reproducibility, measurement according to the above-described procedure was repeated ten times for the same sample. For each measurement, the $HbA_{1c}$ value was calculated from the following equation. The resulting ten $HbA_{1c}$ values, their average value and a CV value (%) are listed in Table 3.

$HbA_{1c}$ value (%)=(Area under the peak $P5$)/(Total area under the peaks $P1, P2, P3, P4, P5$ and $P6$)×100

Comparative Example 5

Figure 18:
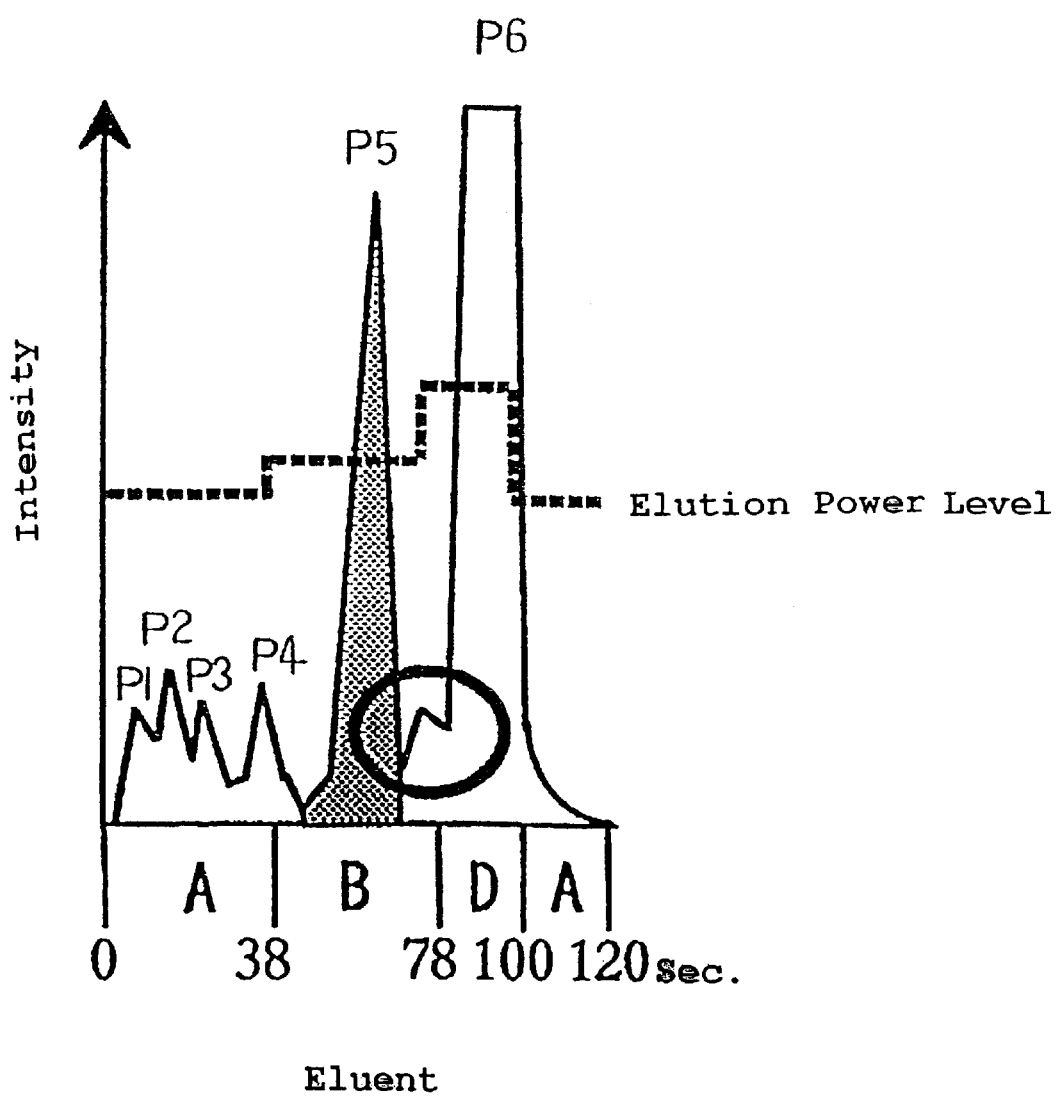
FIG. 18 shows a condition under which the eluents of Comparative Example 5 are sequentially passed through a column and a resulting chromatogram.

Measurement of hemoglobins present in the same sample as used in Example 13 was carried out in the same manner as in Example 13, except that the eluent C was not used. The delivery sequence of the eluents, as well as a resulting chromatogram, are shown in FIG. 18. That is, the eluent A was delivered for an initial 38-second period, the eluent B having a higher elusion power for the next 40-second period, the eluent D having the highest elution power for the next 22-second period and again the eluent A for the final 20-second period. As a result of the increase in elution power when the eluent was changed from A to B, the peak P6 was partially eluted earlier and overlay the peak P5. This is indicated by a circled spot in FIG. 18.

To evaluate reproducibility, measurement according to the above-described procedure was repeated ten times for the same sample. At each measurement, the $HbA_{1c}$ concentration was calculated in the same manner as in Example 1. The resulting ten $HbA_{1c}$ values, their average value and a CV value (%) are listed in Table 3.

Comparative Example 6

Figure 19:
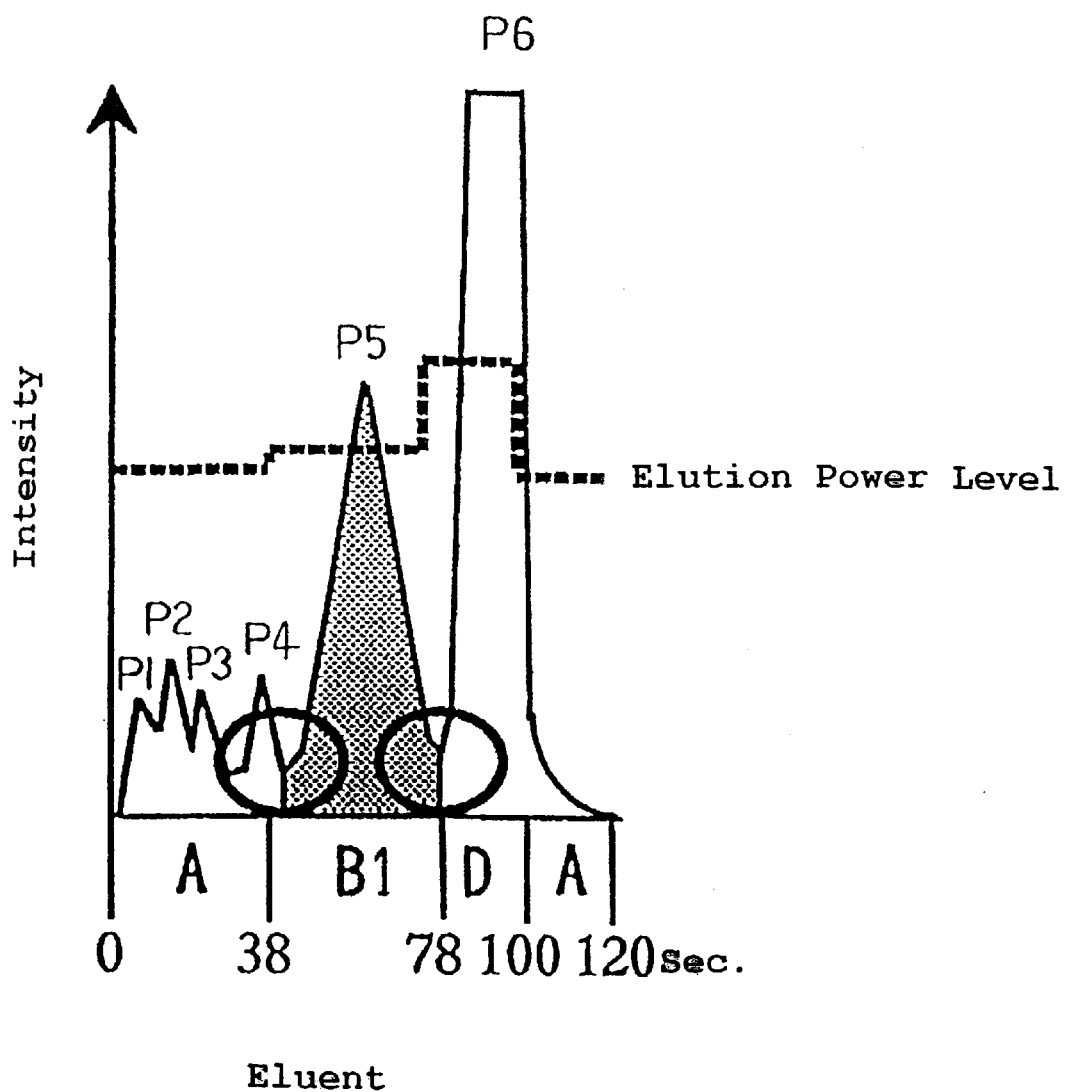
FIG. 19 shows a condition under which the eluents of Comparative Example 6 are sequentially passed through a column and a resulting chromatogram.

Measurement of hemoglobins present in the same sample as used in Example 13 was carried out in the same manner as in Example 13, except that the eluent C was not used and the eluent B was replaced by the eluent B1 (180 mM phosphate buffer with a pH of 6). The delivery sequence of the eluents, as well as a resulting chromatogram, are shown in FIG. 19. That is, the eluent A was delivered for an initial 38-second period, the eluent B1 for the next 40-second period, the eluent D having the highest elution power for the next 22-second period and again the eluent A for the final 20-second period. Because the eluent A was changed to the eluent BE having a lower elution power than the eluent B, the earlier elution of a part of the peak P6 was avoided. However, the peak P5 became less sharp and was partially overlaid by the peaks P4 and P6. This is indicated by circled spots in FIG. 19.

To evaluate reproducibility, measurement according to the above-described procedure was repeated ten times for the same sample. For each measurement, the $HbA_{1c}$ value was calculated in the same manner as in Example 1. The resulting ten $HbA_{1c}$ values, their average value and a CV value (%) are listed in Table 3.

TABLE 3

|  | Ex.13 | Comp.Ex.5 | Comp.Ex.6 |
| --- | --- | --- | --- |
| Measured | 4.55 | 4.60 | 4.28 |
| Values (%) | 4.58 | 4.45 | 4.58 |
|  | 4.58 | 4.44 | 4.33 |
|  | 4.58 | 4.58 | 4.36 |
|  | 4.52 | 4.44 | 4.60 |
|  | 4.56 | 4.38 | 4.52 |
|  | 4.55 | 4.45 | 4.55 |
|  | 4.52 | 4.56 | 4.32 |
|  | 4.53 | 4.38 | 4.45 |
|  | 4.55 | 4.55 | 4.60 |
| Mean Value (%) | 4.55 | 4.48 | 4.46 |
| Coefficient of Variation (%) | 0.5 | 1.8 | 2.8 |

EXAMPLE 14

2.0 g of benzoyl peroxide was allowed to dissolve in 450 g of tetraethylene glycol dimethacrylate (product of Shin-Nakamura Chem. Co., Ltd.). The mixture was dispersed in 2.5 L of a 4 wt. % aqueous solution of polyvinyl alcohol.

The resulting dispersion was heated with agitation under a nitrogen atmosphere and allowed to polymerize at 80° C. for 1.5 hours and then cooled to 35° C. After addition of 200 g of 2-acrylamide-2-methylpropanesulfonic acid (product of Tokyo Chemical Ind. Co., Ltd.) and the following 1-hour agitation, the reaction system was again allowed to polymerize at 80° C. for 1.3 hours.

The resulting polymers were washed and classified to obtain a packing material with a mean particle diameter of 6.5 µm.

Comparative Example 7

400 g of 2-hydroxyethyl methacrylate (product of Shin-Nakamura Chem. Ind. Co., Ltd.), 50 g of diethylene glycol dimeth-acrylate, 50 g of methyl methacrylate and 1.5 g of benzoyl peroxide were mixed and then dispersed in 2.5 L of a 4 wt. % aqueous solution of polyvinyl alcohol. The dispersion was heated with agitation under a nitrogen atmosphere and allowed to polymerize at 80° C. for 8 hours.

The resulting polymers were washed and classified to obtain polymer particles with a mean particle diameter of 2.9 µm. 100 g of the polymer particles was dispersed in 100 mL of a 20 wt. % aqueous solution of sodium hydroxide. 40 g of epichlorohydrin was added to the dispersion which was subsequently allowed to react for 5 hours. 100 g of the resulting epoxy-containing polymer particles was dispersed in 100 mL of a 20 wt. % aqueous solution of sodium sulfate and then allowed to polymerize at 80° C. for 15 hours. The resulting polymer particles were washed and dried to obtain packing material.

Comparative Example 8

2.5 g of benzoyl peroxide was allowed to dissolve in 125 g of ethylene glycol dimethacrylate (product of Shin-Nakamura Chem. Ind. Co., Ltd.). The mixture was dispersed in 2.5 L of a 4 wt. % aqueous solution of polyvinyl alcohol and then heated with agitation under a nitrogen atmosphere to 80° C. After the lapse of 1 hour, 125 g of 2-acrylamide-2-methylpropane-sulfonic acid was added to the reaction system which was subsequently allowed to further polymerize at 80° C. for 24 hours.

The resulting polymers were washed and classified to obtain packing material with a mean particle diameter of 6.5 µm.

(Evaluation)

(1) Evaluation of Physical Properties

The packing materials, after dried, were evaluated for the below-described physical properties. The pore size distribution, specific surface area and pore volume were measured according to a gas adsorption technique by a high-perfomance specific surface area/pore size distribution measuring equipment (NOVA-1200, manufactured by Yuasa Ionics Co., Ltd.). The ion exchange capacity was determined by a potentiometric titration equipment (AT-310, manufactured by Kyoto Electronic Ind. Co., Ltd.). The measurement results are given in Table 4.

TABLE 4

|  | Physical Properties | | | |
| --- | --- | --- | --- | --- |
|  | Pore Diameter (Å) | Specific Surface Area (m²/g) | Pore Volume (µl/g) | Ion Exchange Capacity (µeq/g) |
| Ex.14 | 60 | 0.68 | 1.02 | 65 |
| Comp.Ex.7 | <10 | 5.6 | 0.31 | 75 |
| COmp.Ex.8 | 74 | 0.96 | 12.1 | 185 |

(2) Packing of the Material into a Column 0.7 g of each packing material was dispersed in 30 mL of a 50 mM phosphate buffer (pH 6.0), subjected to an ultrasonic treatment for 5 minutes and stirred well. The whole content was injected into a packer (product of Umetani Seiki Co., Ltd.) connected to a vacant stainless steel column (inner diameter 4.6×35 mm). The content was packed under a constant pressure of 200 kg/cm² into the column by means of a delivery pump (product of Sanuki Ind. Co., Ltd.) connected to the packer.

(Measurement Conditions)

Measurement of hemoglobins was carried out in the same manner as in Example 1, with the exception that the eluents having the following compositions were used.

Eluents:
    eluent E: 15–100 mM phosphate buffer (pH 5.0–6.0) containing perchlorate
    eluent F: 300 mM phosphate buffer (pH 7.0– 8.5) containing perchlorate Measurement of hemoglobins was carried out according to a stepwise gradient elution technique, while achieving optimization of $HbA_{1c}$ retention time by adjusting the salt concentrations and pH's of the eluents E and F to fall within the above-specified respective ranges.

(Measurement Results)

Figure 20:
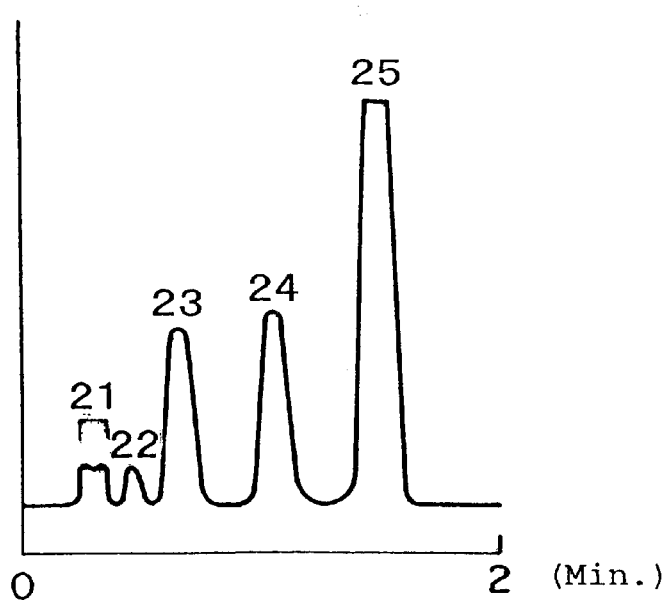
FIG. 20 is a chromatogram obtained when determination of hemoglobins was carried out utilizing the packing material obtained in Example 14.
Figure 21:
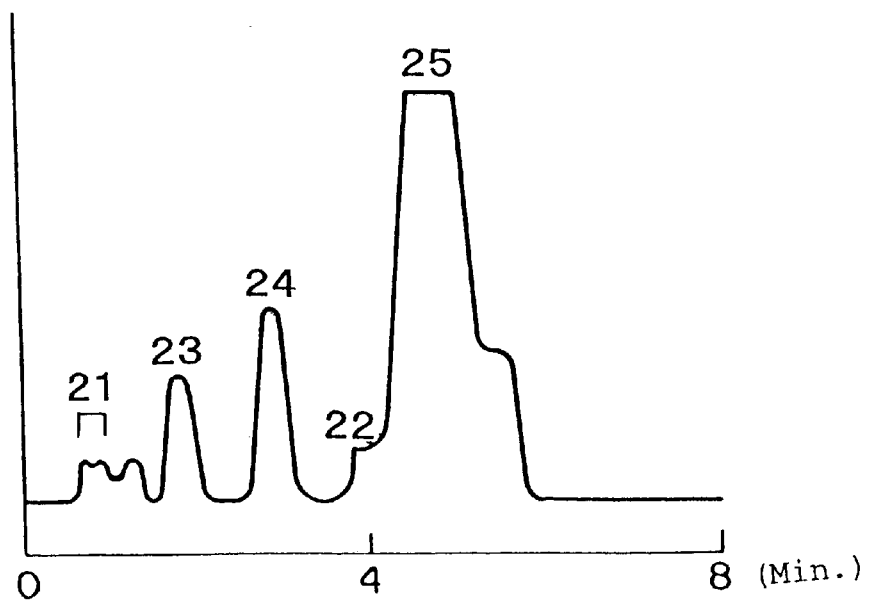
FIG. 21 is a chromatogram obtained when determination of hemoglobins was carried out utilizing the packing material obtained in Comparative Example 7.
Figure 22:
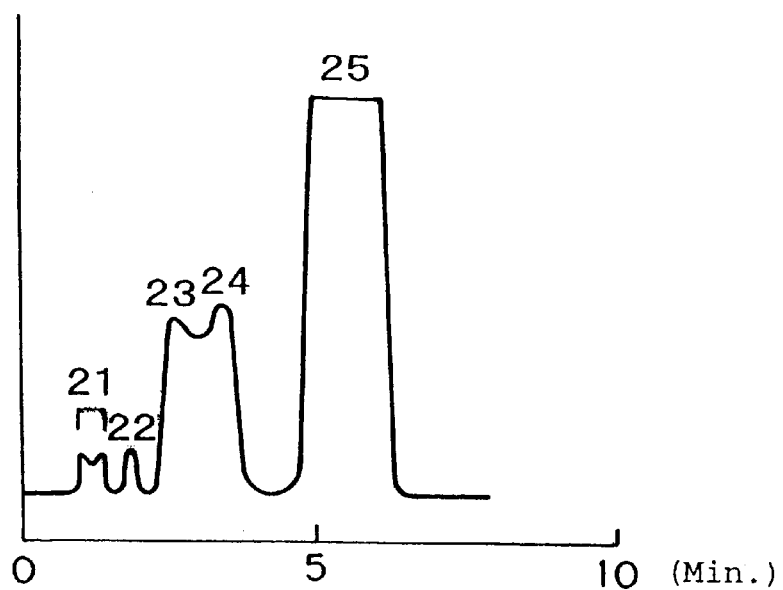
FIG. 22 is a chromatogram obtained when determination of hemoglobins was carried out utilizing the packing material obtained in Comparative Example 8.

Measurement of the sample a was carried out using the packing materials obtained in Example 14 and Comparative Examples 7 and 8. Their results are shown in FIGS. 20, 21 and 22, respectively.

In FIGS. 20–24, reference numerals applied to peaks represent the followings.

21 . . . $HbA_{1a}$ and $HbA_{1b}$
22 . . . HbF
23 . . . labile $HbA_{1c}$
24 . . . stable $HbA_{1c}$
25 . . . $HbA_0$
26 . . . $HbA_2$
27 . . . HbS and HbC In order for HbF and stable $HbA_{1c}$ to be quantitated in a satisfactory manner, hemoglobin elution must proceed in the order of HbF, labile $HbA_{1c}$, stable $HbA_{1c}$ and $HbA_0$. This is because it will become extremely defficult to quantitate HbF if it is eluted, for example, between stable $HbA_{1c}$ and $HbA_0$ whose peaks are more intense than the HbF peak.

In the case where the packing material of Example 14 was used, peaks appeared in the above-described order and were well separated in spite of the shortend measurement time.

However, in the case where the packing material of Comparative Example 7 was used, the elution sequence was altered to make HbF and stable $HbA_{1c}$ less determinable. The packing materials obtained in Comparative Example 7 and 8 revealed poor separation in spite of the extended measurement time.

(5) Measurement of Abnormal Hb's

Figure 23:
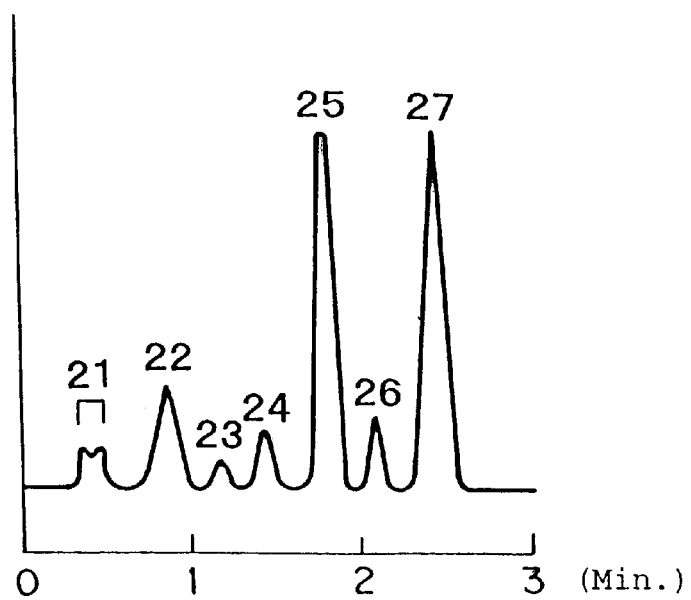
FIG. 23 is a chromatogram obtained when determination of abnormal hemoglobins was carried out utilizing the packing material obtained in Example 14.
Figure 24:
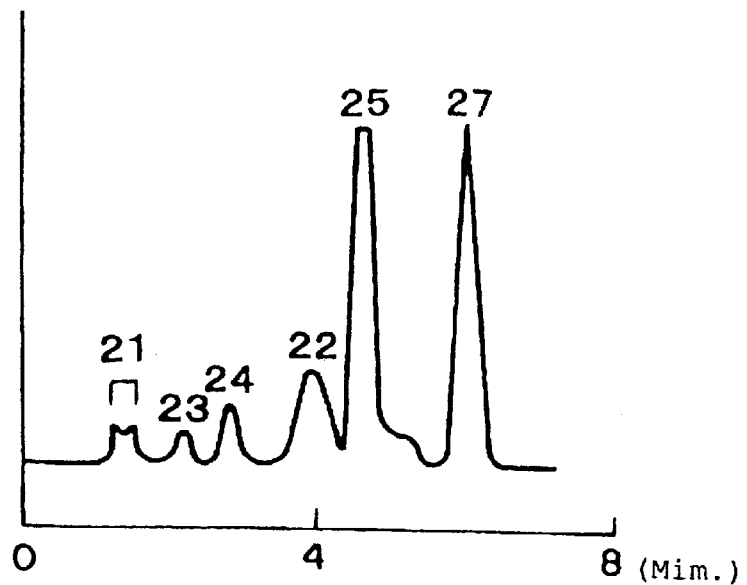
FIG. 24 is a chromatogram obtained when determination of abnormal hemoglobins was carried out utilizing the packing material obtained in Comparative Example 7.

A sample was prepared by subjecting a control blood (AFSC Control, product of Helena) containing $HbA_2$, HbS and HbC, as abnormal hemoglobins, to 67-fold hemolytical dilution with a hemolyzing reagent, and measured under the same conditions. The packing materials of Example 14 and Comparative Example 7 were used for the measurement. The results are shown in FIGS. 23 and 24, respectively. Notwithstanding the shortened measurement time, the packing material of Example 14 revealed superior peak separation compared to the packing material of Comparative Example 7.

(6) Column Life Test

A sample was prepared by subjecting a whole blood to 150-fold hemolytical dilution with a hemolyzing reagent, and measured repeatedly under the same conditions as described above to observe the variation of stable $HbA_{1c}$ value.

The stable $HbA_{1c}$ value was calculated as follow:

Stable $HbA_{1c}$ value (%)=(peak area of stable $HbA_{1c}$)/(total peak area)×100.

Figure 25:
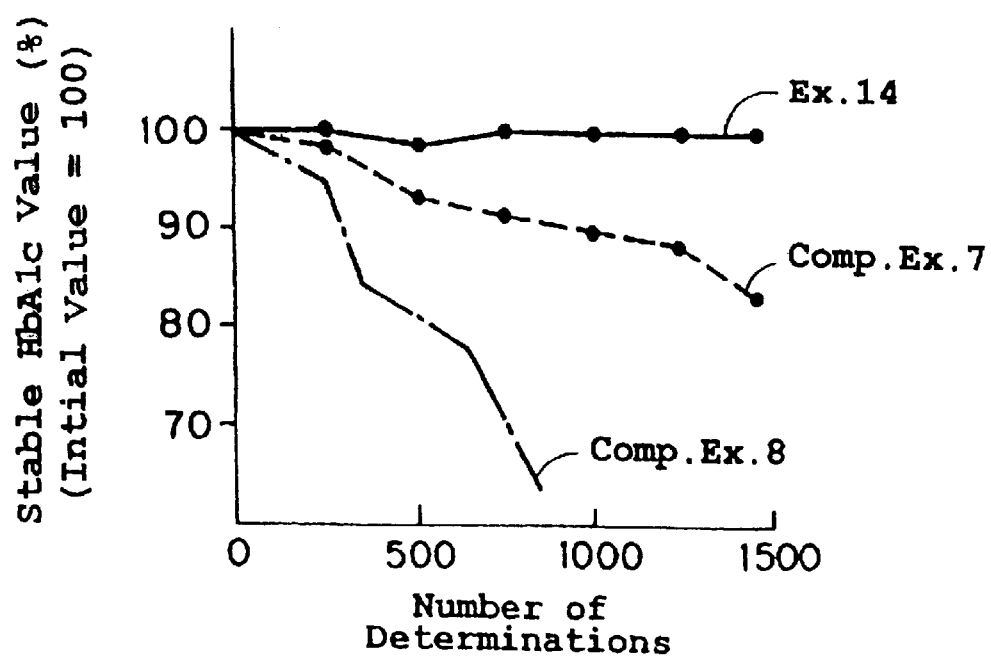
FIG. 25 is a graph showing the column durability test results with the use of the packing materials obtained in Example 14, Comparative Examples 7 and 8.

The results are shown in FIG. 25. Measurement values were maintained unvaried for a longer period of time with the use of the packing material of Example 14 than the packing materials of Comparative Examples 7 and 8.

(7) Reproducibility Test

For each of the packing materials obtained in Example 14 and Comparative Examples 7 and 8, 30 units (30 lots) were prepared under identical conditions. Using these lots, measurement of a whole blood specimen was performed under the same conditions as described above. The eluents were controlled so that a retention time of stable $HbA_{1c}$ recorded about 5.0 minutes. As can be appreciated from the variations in stable $HbA_{1c}$ retention time and stable $HbA_{1c}$ value between lots, as shown in Table 5, the packing material of Example 14 exhibited the higher reproducibility compared to the packing materials of Comparative Examples 7 and 8. For the packing material of Comparative Example 8, seven lots, out of 30 lots, were accompanied by production of aggregates, during polymerization, which prevented their packing into a column.

TABLE 5

|  | Number of Lots | Retention Time of Stable HbAlc (Min.) | Stable HbAlc Value (%) |
| --- | --- | --- | --- |
| Ex.14 | 30 | 5.0 ± 0.4 | 4.7 ± 0.2 |
| Comp.Ex.7 | 30 | 5.1 ± 1.2 | 4.8 ± 1.1 |
| Comp.Ex.8 | 23 | 5.0 ± 3.6 | 2.4 ± 1.5 |

EXAMPLE 15

An equiweight mixture of polyether ether ketone and a fluorine resin was sintered in a mold to produce an integral filter 11 shown in FIG. 26(a). The filter was constructed in a cylindrical configuration having a diameter of 5 mm and a thickness of 1.5 mm, with a pore size of 2 $\mu$m.

Figure 27:
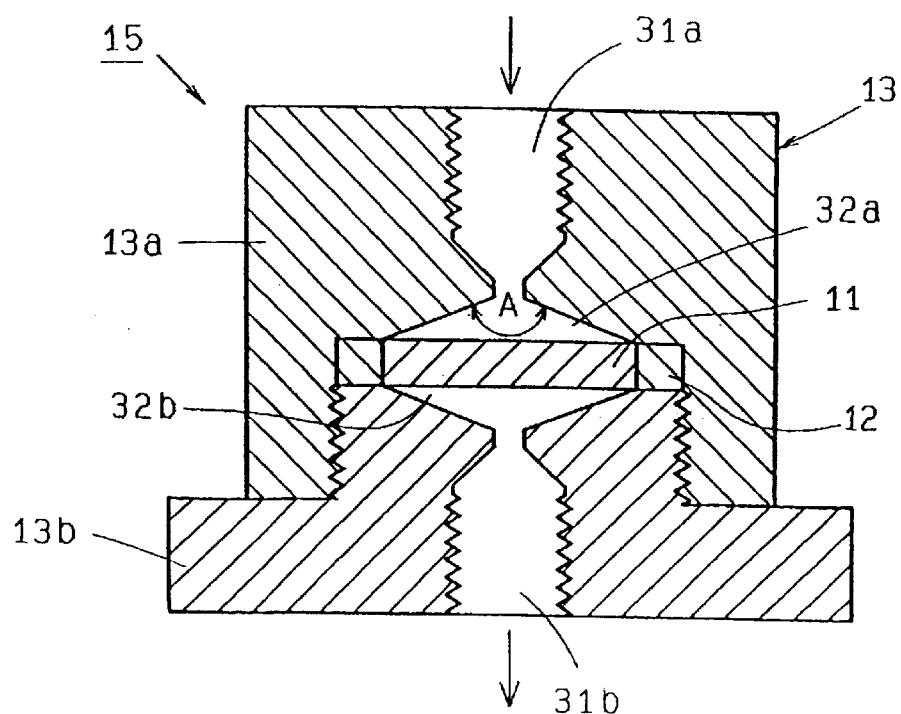
FIG. 27 is a sectional view of a line filter which incorporates the filter of the present invention fitted in a holder.
Figure 28:
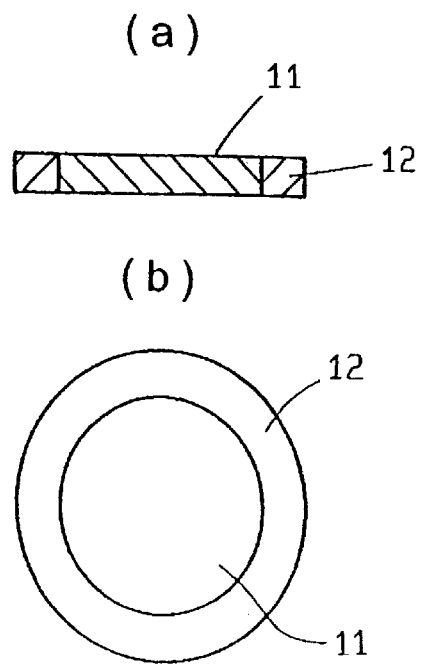
FIGS. 28(a) and (b) are a sectional view and a plan view of the LC filter of the present invention, respectively.

The filter 11 was inserted in a seal member 12 composed of polyether ether ketone and then fitted in a stainless steel holder 13 (vertical angle A=90 degrees), as shown in FIG. 27. Subsequently, halves 13a and 13b were connected to each other along screw threads. As a result, a line filter 15 was assembled.

EXAMPLE 16

An integral filter 11 made in the same manner as in Example 15 was inserted in a seal member 12 composed of polyether ether ketone and then fitted in a holder 13 (vertical angle A=150 degrees) also composed of polyether ether ketone. Subsequently, halves 13a and 13b were connected to each other along screw threads. As a result, a line filter 15 was assembled.

EXAMPLE 17

Polyethylene was sintered in a mold to produce an integral filter 11 shown in FIG. 26(a). The filter was constructed in a cylindrical configuration having a diameter of 5 mm and a thickness of 1.5 mm, with a pore size of 2 $\mu$m.

The filter 11 was inserted in a seal member 12 composed of polyether ether ketone and then fitted in a holder 13 (vertical angle A=150 degrees) also composed of polyether ether ketone, as shown in FIG. 27. Subsequently, halves 13a and 13b were connected to each other along screw threads. As a result, a line filter 15 was assembled.

Comparative Example 9

Metal powders were sintered in a mold to produce an integral stainless steel filter 11 shown in FIG. 26(a). The filter was constructed in a cylindrical configuration having a diameter of 5 mm and a thickness of 1.5 mm, with a pore size of 2 $\mu$m.

The filter 11 was inserted in a seal member 12 formed of a fluorine resin and then fitted in a stainless steel holder 13 (vertical angle A=90 degrees). Subsequently, halves 13a and 13b were connected to each other along screw threads. As a result, a line filter 15 was assembled.

Using the line filters assembled in Examples 15–17 and Comparative Example 9, (1) biosample adsorptivity and (2)

the relationship between the biosample adsorptivity and the eluent pH (pH 5.0, pH 6.0 and pH 7.0) were evaluated according to the following procedures.

(1) Evaluation of Adsorptivity

In order to evaluate the biosample adsorptivity, measurement of hemoglobins was carried out in the same manner as in Example 1, except that the compositions and delivery sequence of eluents were altered to those specified below and that the line filters assembled in Examples 15–17 and Comparative Example 9 were used alone (i.e., without using a column). The sample a in Example 1 was used as a measurement sample.

(Measurement Conditions)

Eluents:
   eluent A: 100 mM phosphate buffer (pH 5.8)
   eluent B: 300 mM phosphate buffer (pH 6.8)

The elunt A was delivered for the initial 3-minute period, the eluent B for the subsequent 2-minute period and again the eluent A for the final 5-minute period.

(Measurement Results)

Figure 30:
FIGS. 30A, 30B, and 30C are chromatograms obtained when measurement of a sample was carried out (a) without the use of the line filter, (b) with the use of the line filters of Examples 15–17, and (c) with the use of the line filter of Comparative Example 9.
Figure 30:
Figure 30:
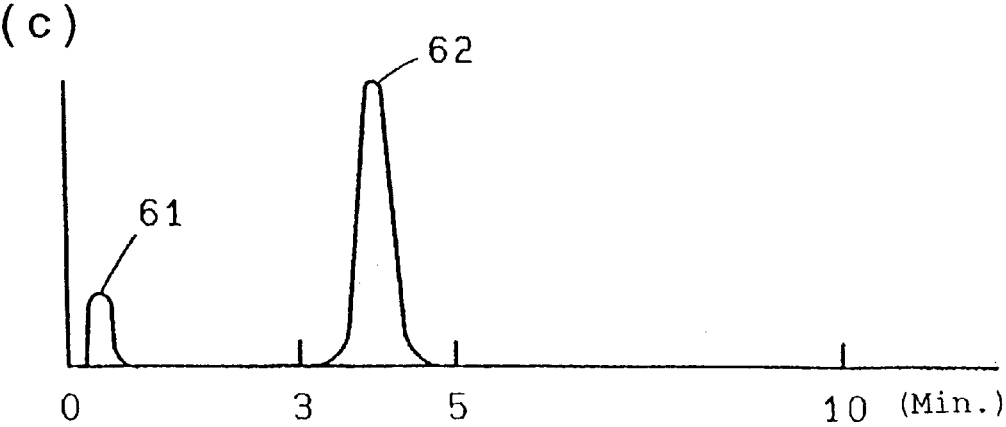

Typical chromatrgrams resulted from measurement of the sample under the above-described measurement conditions are shown in FIG. 30(a) (no line filter was used), FIG. 30(b) (the line filters of Examples 15–17 were used), and FIG. 30(c) (the line filter of Comparative Example 9 was used). A peak 61 indicates a hemoglobin peak (a single peak appeared due to the absence of column separation). The appearance of a peak 62 is considered due to the desorption by the eluent B of hemoglobins once adsorbed to the filter by the involvement of the eluent A.

Evaluation Method

An area of a hemoglobin peak produced when measurement of the sample was carried out without a line filter was recorded as 100%. Taking this as a control, an area of a hemoglobin peak (an area of each peak 61) produced with the use of each of the line filters assembled in Examples 15–17 and Comparative Example 9 was calculated. Then, a recovery (%) of hemoglobin by the eluent A was calculated from the following equation. The results are given in Table 6. Measurement was repeated three times for each line filter.

Recovery (%)=(area of a hemoglobin peak produced when each line filter was attached)/(area of a hemoglobin peak produced when no line filter was attached)×100

Although Comparative Example 9 revealed an average recovery of 57.4%, Examples 15–17 revealed average recoveries of 95.3%, 98.5% and 98.0%, respectively.

These results demonstate that the hemoglobin adsorption was reduced by utilizing the line filters of Examples 15–17 compared to utilizing the line filter of Comparative Example 9.

TABLE 6

| No. | Ex.15 | Ex.16 | Ex.17 | Ex.21 | Comp. Ex.9 |
|---|---|---|---|---|---|
| 1 | 94.1 | 98.7 | 97.9 | 96.1 | 50.9 |
| 2 | 96.4 | 97.8 | 97.9 | 97.3 | 57.8 |
| 3 | 95.3 | 98.9 | 98.1 | 96.5 | 63.4 |
| Mean Value | 95.3 | 98.5 | 98.0 | 96.6 | 57.4 |
| Standard Deviation | 1.2 | 0.6 | 0.1 | 0.6 | 6.3 |
| CV (%) | 1.2 | 0.6 | 0.1 | 0.6 | 10.9 |

In Table 6 (also in the below-given Table 7), a CV value (%) refers to a coefficient of variation (i.e., CV value (%)=(standard deviation)/(arithmetic mean)×100). The CV value is markedly increased by utiling the line filter of Comparative Example 9 compared to utilizing the line filters of Examples 15–17. This demonstates that the use of the line filter of Comparative Example 9 results in the increased variation of hemoglobin adsorption.

(2) Evaluation of the Relationship between the Biosample Adsorptivity and the Eluent pH In order to evaluate the relationship between biosample adsorptivity and eluent pH, measurement of hemoglobins was carried out under the same conditions as in the above-described evalution of biosample adsorptivity, except that the pH of the eluent A was varied to pH 5.0, pH 6.0 and pH 7.0. The line filters assembled in Examples 15–17 and Comparative Example 9 were used alone (i.e., no column was used).

Evaluation Method

An area of a hemoglobin peak produced when measurement of the sample was carried out without a line filter was recorded as 100%. Taking this as a control, an area of a hemoglobin peak was calculated from the measurement (n=5) using each of the line filters assembled in Examples 15–17 and Comparative Example 9. Then, a hemoglobin recovery (%) by the eluent A was calculated from the following equation. The results are given in Table 7.

Recovery (%)=(area of a hemoglobin peak produced when each line filter was attached)/(area of a hemoglobin peak produced when no line filter was attached)×100

Comparative Example 9 provided average recoveries of 13.56% at pH 5.0, 76.52% at pH 6.0 and 91.98% at pH 7.0. The CV value (%) increased with a decreasing pH and amounted to 37.27% at pH 5.0.

Example 15 provided average recoveries of 97.42% at pH 5.0, 97.82% at pH 6.0 and 97.20% at pH 7.0.

Example 16 provided average recoveries of 98.56% at pH 5.0, 98.76% at pH 6.0 and 98.82% at pH 7.0.

Example 17 provided average recoveries of 97.72% at pH 5.0, 98.22% at pH 6.0 and 98.46% at pH 7.0.

TABLE 7

| | Comp. Ex. 9 | | | Ex. 15 | | | Ex. 16 | | | Ex. 17 | | |
|---|---|---|---|---|---|---|---|---|---|---|---|---|
| No. | pH 5.0 | pH 6.0 | pH 7.0 | pH 5.0 | pH 6.0 | pH 7.0 | pH 5.0 | pH 6.0 | pH 7.0 | pH 5.0 | pH 6.0 | pH 7.0 |
| 1 | 21.2 | 60.1 | 94.5 | 97.4 | 97.7 | 97.8 | 98.4 | 98.7 | 99.4 | 96.8 | 97.8 | 98.1 |
| 2 | 15.8 | 78.3 | 96.4 | 98.2 | 98.1 | 97.6 | 98.6 | 98.1 | 99.1 | 97.9 | 98.1 | 98.6 |
| 3 | 12.3 | 81.2 | 90.6 | 96.8 | 98.5 | 97.1 | 98.1 | 99.5 | 98.1 | 97.6 | 98.9 | 98.1 |
| 4 | 9.4 | 83.5 | 93.4 | 97.6 | 97.4 | 96.8 | 98.2 | 99.4 | 98.4 | 98.1 | 98.2 | 98.4 |
| 5 | 9.1 | 79.5 | 85.1 | 97.1 | 97.4 | 96.7 | 99.5 | 98.1 | 99.1 | 98.2 | 98.1 | 99.1 |
| Mean Value | 13.56 | 76.52 | 91.98 | 97.42 | 97.82 | 97.20 | 98.56 | 98.76 | 98.82 | 97.72 | 98.22 | 98.46 |
| Standard Deviation | 5.05 | 9.38 | 4.40 | 0.53 | 0.48 | 0.48 | 0.56 | 0.68 | 0.54 | 0.56 | 0.41 | 0.42 |
| CV (%) | 37.27 | 12.26 | 4.78 | 0.55 | 0.49 | 0.50 | 0.57 | 0.69 | 0.55 | 0.58 | 0.42 | 0.42 |

The use of Examples 15–17 resulted in CV values of not exceeding 1% at either pH.

As can be appreciated from the precedings, in the case where the stainless steel filter of Comparative Example 9 is used, the hemoglobin adsorptivity depends largely upon the eluent pH. The use of stainless steel filter results in the marked increase in hemoglobin adsorption and wide variation of adsorption percentage. The use of stainless steel filter for measurement of hemoglobins is thus considered to shorten its service life and scatter the measurement data.

Where the filters of Examples 15–17 were used, the hemoglobin absorptivity was found unaffected by the eluent pH, even if varied from 9.0 to near 5.0, and the recovery reached nearly 100%.

The precedings demonstrate that a filter for use in the measurement of hemoglobins is preferably constructed from polyether ether ketone-containing material or polyehtylene which substantially prevents adsorption of hemoglobins over a wide pH range.

EXAMPLE 18

Figure 26:
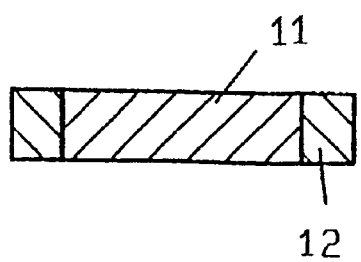
FIGS. 26A, 26B, 26C, 26D, 26E, and 26F are sectional representations of various forms of LC filters according to the present invention.
Figure 26:
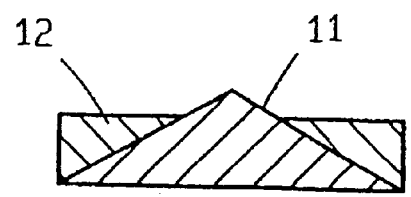
Figure 26:
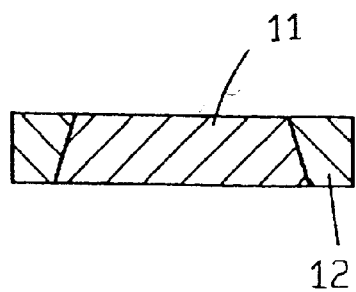
Figure 26:
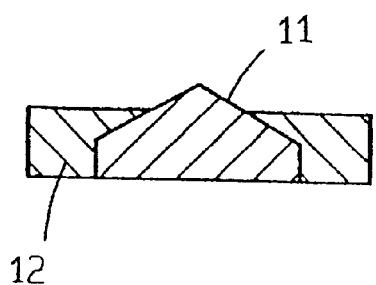
Figure 26:
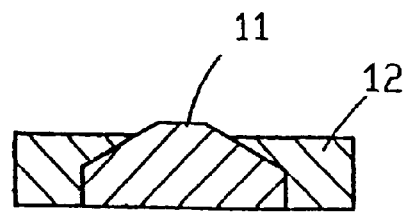
Figure 26:
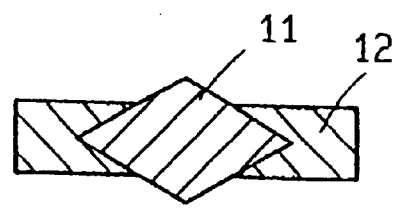
Figure 29:
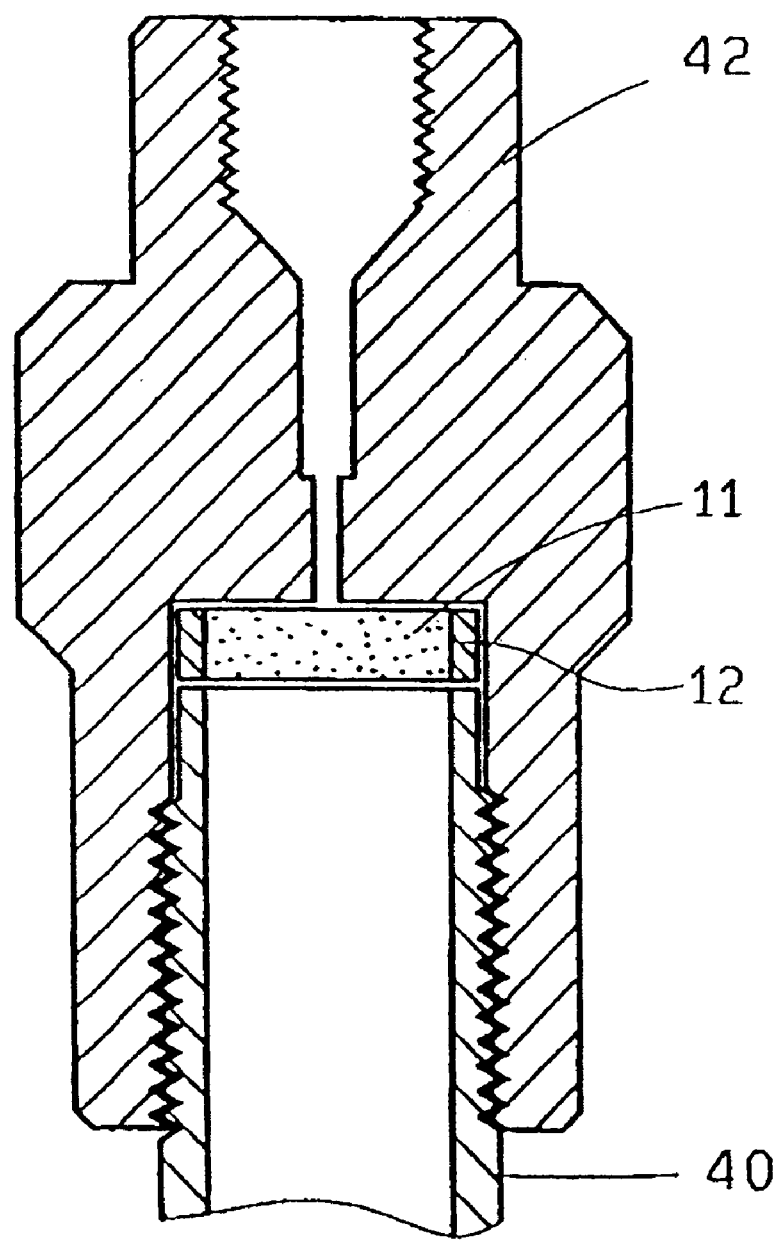
FIG. 29 is a sectional view illustrating the LC column of the present invention.

An equiweight mixture of polyether ether ketone and a fluorine resin was sintered in a mold to produce an integral filter 11 shown in FIG. 26($a$). The filter was constructed in a cylindrical configuration having a diameter of 4.8 mm and a thickness of 2 mm, with a pore size of 2 $\mu$m. The filter 11 was then inserted in a seal member 12 (having an outer diameter of 6.3 mm, an inner diameter of 4.8 mm and a thickness of 2.0 mm) composed of a fluorine resin and subsequently fitted in an end fitting 42 for attachment to each end of a stainless steel column body 40 (having an inner diameter of 4.6 mm and a length of 30 mm) shown in FIG. 29.

The packing material was prepared according to the below-described procedure and then packed into the column according to the procedure as described in the section of "Fabrication of a Column" to fabricate the LC column of the present invention.

Preparation of Packing Material 1.5 g of benzoyl peroxide (polymerization initiator manufactured by Wako Co., Ltd.) was allowed to dissolve in a mixture containing 400 g of tetraethylene glycol dimethacrylate (product of Shin-Nakamura Chem. Ind. Co., Ltd.) and 150 g of methacrylic acid (product of Wako Co., Ltd.). The resulting mixture was dispersed in 2,500 mL of a 4 wt. % aqueous solution of polyvinyl alcohol (Nippon Kagaku Co., Ltd.), heated with agitation under a nitrogen atmosphere to 75° C., and allowed to polymerize for 8 hours. The resulting polymerizate was washed, dried and classified to obtain particles with a mean particle diameter of 6 $\mu$m.

Fabrication of a Column

For each column, 1.0 g of the above-prepared packing material was dispersed in 30 mL of 50 mM phosphate buffer (pH 6.0). The dispersion was supersonically treated for 5 minutes and then stirred well. The whole content was poured into a packer (product of Umetani Seiki Co., Ltd.) connected to the stainless steel column body 40 (inner diameter 4.6×30 mm). The content was. packed under a constant pressure of 300 kg/cm$^2$ into the stainless steel column body 40 by means of a delivery pump (product of Sanuki Kogyo Co., Ltd.) connected to the packer. Thereafter, the end fitting 42 and column body 40 were connected to each other along secrew threads. As a result, the LC column of the present invention was assembled.

EXAMPLE 19

The procedure of Example 18 was followed, with the exception that polyethylene, instead of the equiweight mixture of polyether ether ketone and a fluorine resin, was sintered in a mold to produce the integral filter 11, to fabricate an LC column.

Comparative Example 10

The procedure of Example 18 was followed, with the exception that metal powders, instead of the equiweight mixture of polyether ether ketone and a fluorine resin, were sintered in a mold to produce the integral stainless steel filter 11, to fabricate an LC column.

Measurement of hemoglobins was carried out under the folloiwng conditions utilizing the columns obtained in Examples 18 and 19 and Comparative Example 10 (but excepting a line filter) to evaluate their separation performances.

Measurement Conditions

Measurement of hemoglobins was carried out in the same manner as in Example 1, with the exception that the flow rate was controlled at 1.6 mL/min and the compositions and delivery sequence of eluents were altered to those specified below. The sample a in Example 1 was used as a measurement sample.

Eluents:

eluent A: 100 mM phosphate buffer (pH 5.8)

eluent B: 300 mM phosphate buffer (pH 6.8)

The elunt A was delivered for the initial 5-minute period, the eluent B for the subsequent 1-minute period and again the eluent A for the final 4-minute period.

Measurement Results

Figure 31:
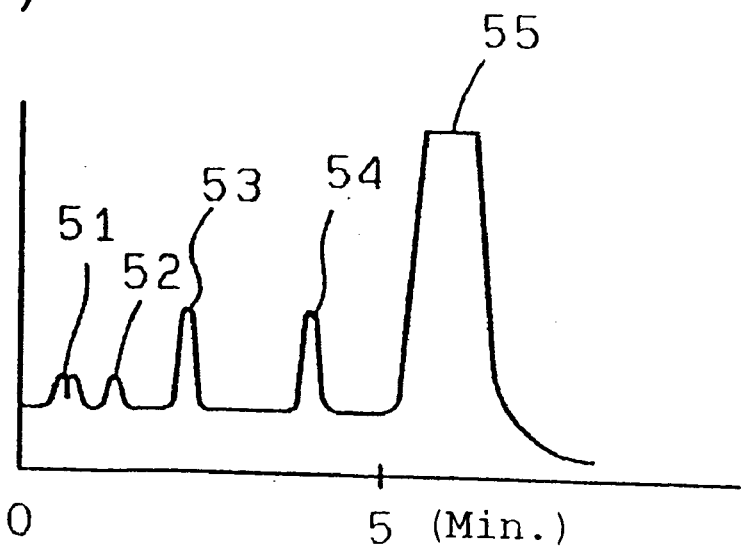
FIGS. 31A and 31B are chromatograms obtained when measurement of a sample was performed (a) with the use of the column of Example 18 and (b) with the use of the column of Comparative Example 10.
Figure 31:
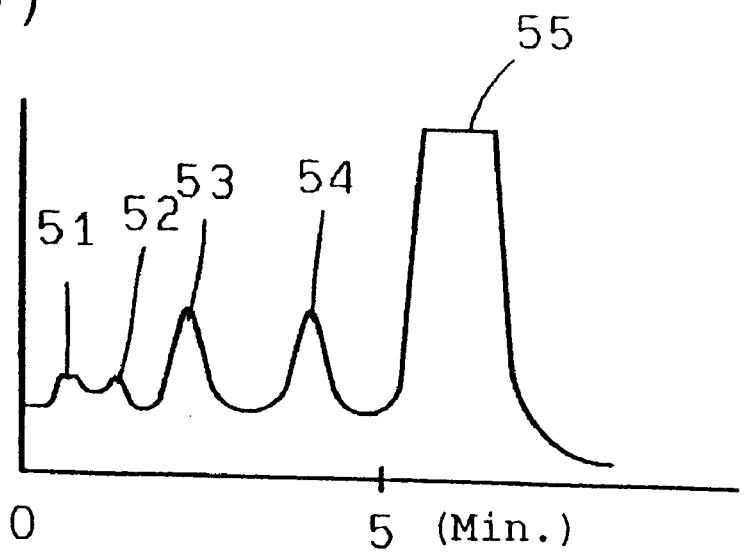
Figure 32:
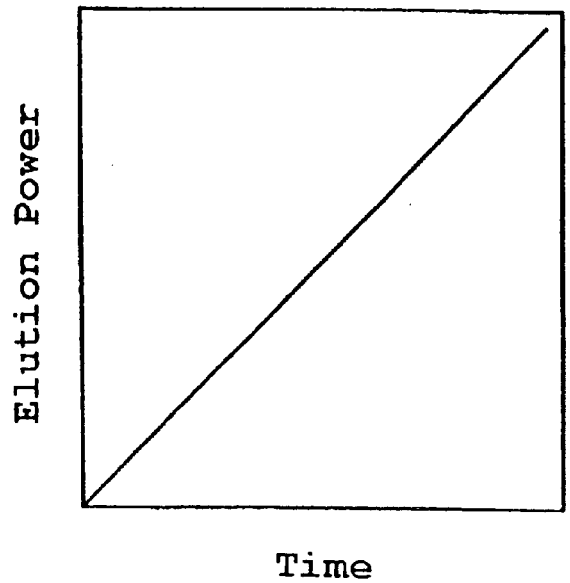
FIG. 32 is a graph for explaining the gradient elution process.
Figure 33:
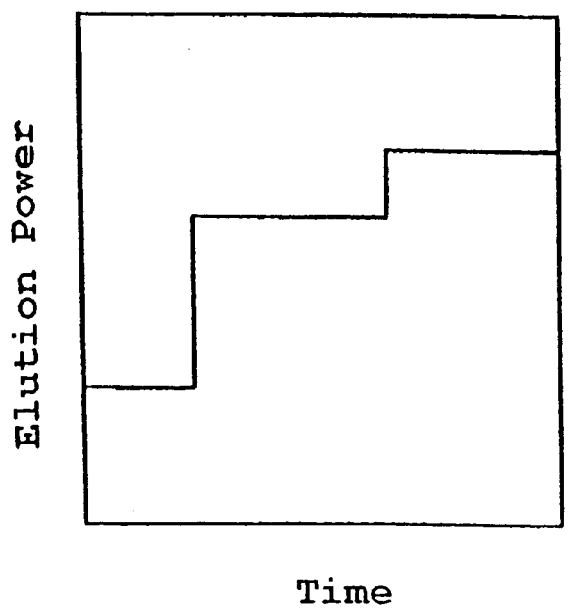
FIG. 33 is a graph for explaning the stepwise elution process.

The chromatrgrams obtained via measurement of the sample under the above-specified conditions are shown in FIG. 31($a$) (the column of Example 18 was used) and in FIG. 31($b$) (the column of Comparative Example 10 was. used). Peak 51 represents HbA$_{1a}$ and HbA$_{1b}$. Peaks 52, 53, 54 and 55 represent HbF, labile HbA$_{1c}$, stable HbA$_{1c}$ and HbA$_0$, respectively. As can be clearly seen from the results, the liquid chromatographic column of Example 18 exhibits the improved separation performance compared to the liquid chromatographic column of Comparative Example 10. The column of Example 19 was also found to achieve good separation in a manner similar to the column of Example 18.

EXAMPLE 20

Measurement of Hb's (sample a) was carried out in the same manner as in Comparative Example 2, with the exception that the following hemolyzing reagent was used.

(Hemolyzing Reagent)

Guanidine was added to a phosphate buffer solution (pH 7.0) (standard hymolyzing reagent) containing 0.1 wt. % polyethylene glycol mono-4-octylphenyl ether (Triton X-100) to a concentration of 100 mM.

(Measurement Results)

The chromatogram obtained was similar to that shown in FIG. 1. As can be appreciated from comparison to the chromatogram (FIG. 4) of Comaprative Example 2, the improved separation of each peak resulted.

EXAMPLE 21

The recovery of hemoglobins was evaluated in the same manner as described above using the stainless steel filter of the above Comparative Example 9, with the exception that the following eluents were used.

(Eluents)

Eluent A: 100 mM phosphate buffer (pH 5.8) containing 100 ppm 2-aminoethanol

Eluent B: 300 mM phosphate buffer (pH 6.8)
(Measurement Results)

The recovery was shown in Table 6. Although the use of the line filter of Comparative Example 9 resulted in a low recovery, the addition of amines achieved a marked recovery improvement.

EXAMPLE 22

(Preparation of Packing Material)

2.0 g of benzoyl peroxide was mixed and allowed to dissolve in a mixture containing 450 g of tetraethylene glycol dimethacrylate (product of Shin-Nakamura Chem. Ind. Co., Ltd.) and 50 g of 2-hydroxy-1,3-methacryloxypropane. The resulting mixture was dispersed in 2.5 L of a 4 wt. % aqueous solution of polyvinyl alcohol.

The dispersion was then heated with agitation under a nitrogen atmosphere and allowed to polymerize at 80° C. for 1.5 hours. The reaction system was subsequently cooled to 35° C. Thereafter, 400 g of a 50% aqueous solution of 2-acrylamide-2-methylpropanesufonic acid (product of Tokyo Chemical Ind. Co., Ltd.) and 400 mL of methanol were added to the reaction system which was subsequently stirred for 1 hour and again allowed to polymerize at 80° C. for 1.3 hours.

The resulting polymerizate was washed and classified to obtain packing material with a mean particle diameter of 6.5 $\mu$m. The material was packed in a column in the manner as described above.

By utilizing the column obtained, measurement of Hb's was preformed under the following conditions.

(System) The system was identical to that employed in Example 1.

(Line Filter) The polyethylene line filter of Example 17 was used.

(Packing of the Material into the Column) The procedure of Example 1 was followed. After the packing, a 170 mM phosphate buffer (pH 5.7) containing 0.3 wt. % Hb reagent (product of Difco Laboratories) was passed through the column at a flow rate of 1.5 mL/min for a period of 15 minutes. Subsequently, a 170 mM phosphate buffer (pH 5.7) was passed through the column for a period of 15 minutes. This enabled speedy stabilization of measurements during an early stage.

(Other Conditions)

Detection wavelength: 415 nm

Flow rate: 1.8 mL/min

Sample injection: 10 $\mu$L (Samples)

The samples a–c described in Example 1, as well as the abnormal Hb control blood in Example 14, were used.

(Measurement of Samples a–c)
(Measurement Conditions)
(Eluents) The following three types of eluents were used.
Eluent A: 20 mM succinate-20 mM phosphate buffer (pH 5.3) containing 55 mM perchloric acid
Eluent B: 20 mM succinate-20 mM phosphate buffer (pH 5.3) containing 70 mM perchloric acid
Eluent C: 20 mM succinate-20 mM phosphate buffer (pH 8.0) containing 250 mM perchloric acid (Delivery Condition) In accordance with the stepwise gradient elution technique, the eluents were selectively delivered at the follwing time intervals.

0–38 seconds: eluent A
38–58 seconds: eluent B
58–78 seconds: eluent A
78–100 seconds: eluent C
100–120 seconds: eluent A
(Measurement Results)

Figure 34:
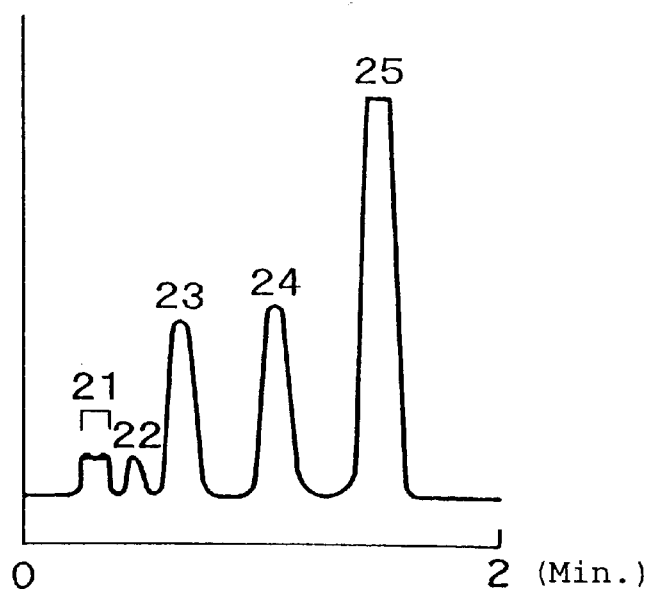
FIG. 34 is a chromatogram obtained when determination of hemoglobins (sample a) was performed under the conditions of Example 22.
Figure 35:
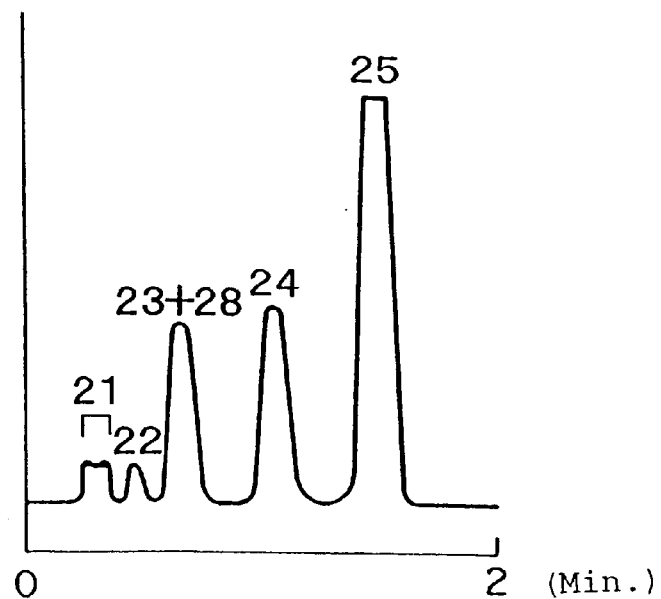
FIG. 35 is a chromatogram obtained when determination of hemoglobins (sample b) was performed under the conditions of Example 22.
Figure 36:
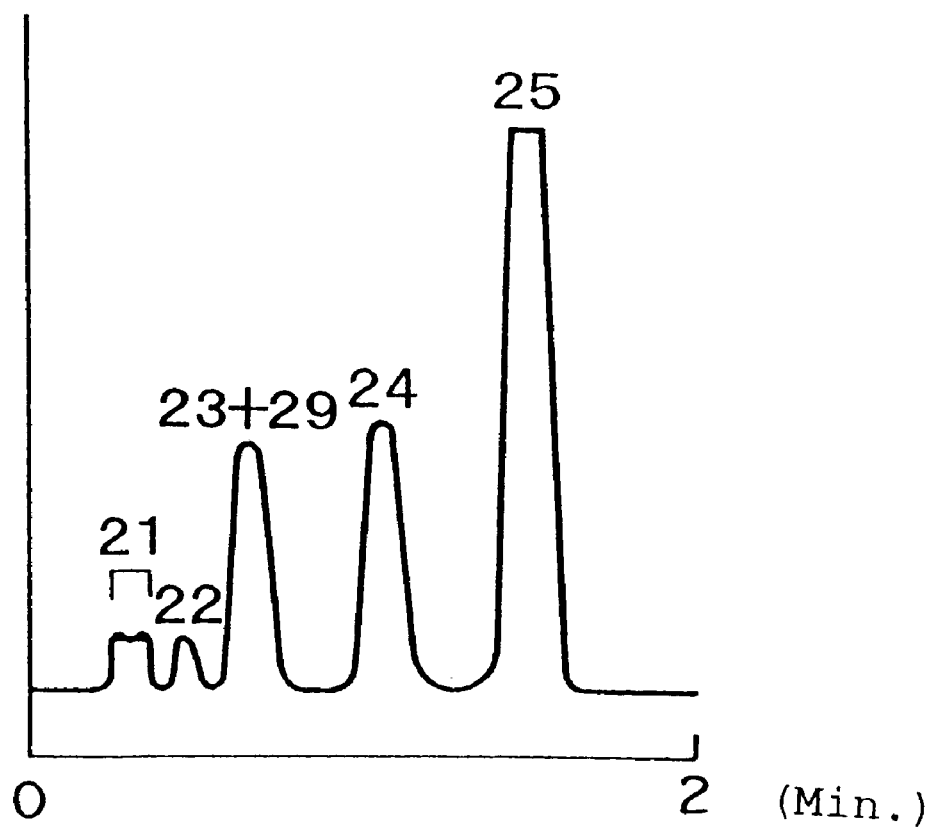
FIG. 36 is a chromatogram obtained when determination of hemoglobins (sample c) was performed under the conditions of Example 22.

The measurement results of the samples a–c are given in FIGS. 34–36, respectively. In FIGS. 34–36, Peaks 21–25 represent the same hemoglobin types as in Example 14. Peaks 28 and 29 represent CHb and AHb, respectively.

In FIG. 34, labile $HbA_{1c}$ and stable $HbA_{1c}$ are well separated. Peak 28 (CHb) is well separated from Peak 24 in FIG. 35. Peak 29 (AHb) is well separated from Peak 24 in FIG. 36.

(Measurement of Abnormal Hb containing Samples)
(Measurement Conditions)
(Eluents) The following four types of eluents were used.
Eluent A: 20 mM succinate-20 mM phosphate buffer (pH 5.3) containing 55 mM perchloric acid
Eluent B: 20 mM succinate-20 mM phosphate buffer (pH 5.3) containing 70 mM perchloric acid
Eluent C: 20 mM succinate-20 mM phosphate buffer (pH 8.0) containing 250 mM perchloric acid
Eluent D: 20 mM succinate-20 mM phosphate buffer (pH 6.8) containing 70 mM perchloric acid (Delivery Condition) In accordance with the stepwise gradient elution technique, the eluents were selectively delivered at the following time intervals.

0–38 seconds: eluent A
38–58 seconds: eluent B
58–78 seconds: eluent A
78–120 seconds: eluent D
120–140 seconds: eluent C
140–180 seconds: eluent A
(Measurement Results)

The chromatogram obtained was similar to that shown in FIG. 23. Following $HbA_0$, each abnormal Hb was separated well.

Effects of the Invention

With the use of the methods for determining hemoglobins according to the first and second inventions of the present application, the hemoglobin separation performance can be improved which has been the problem encountered in the previous methods for determining hemoglobins. Particularly, stable $HbA_{1c}$ can be separated with high reproducibility and precision.

What is claimed is:

1. A method for determining hemoglobins by a cation exchange LC characterized by the use of an eluent containing at least one chaotropic ion selected from the group consisting of tribromo acetate, trichloro acetate, thiocyanate, iodide, perchlorate, dichloroacetate, nitrate, bromide, barium, cesium and guanidine ions, and further an inorganic acid, an organic acid and/or any salt thereof having a buffer capacity in the 4.0–6.8 pH range.

2. A method for determining hemoglobins by a cation exchange LC characterized by the use of an eluent containing at least one chaotropic ion selected from the group consisting of tribromo acetate, trichloro acetate, thiocyanate, iodide, perchlorate, dichloroacetate, nitrate, bromide, barium, cesium and guanidine ions, and a buffer agent having acid dissociation constants (pKa) in the range of 2.15–6.39 and in the range of 6.40–10.50.

3. The method for determining hemoglobins as recited in claim 1, characterized in that the eluent, when enters a column, has a pH equal to or shifted to an alkaline side than an isoelectric point of hemoglobin so that $HbA_0$ can be eluted.

4. The method for determining hemoglobins as recited in claim 3, characterized in that the pH of said eluent is at least 6.8.

5. The method for determining hemoglobins of claim 1, wherein at least three types of eluents having different elution powers are used and that, before one type of eluent purposed to elute $HbA_0$ is delivered, the other types of eluents are delivered.

6. The method for determining hemoglobins of claim 1, wherein the eluent is controlled to reduce its elution power in the course of delivering according to a gradient or stepwise gradient elution technique.

7. The method for determining hemoglobins of claim 1, wherein subsequent to elution of $HbA_0$, at least one hemoglobin from the group consisting of $HbA_2$, HbS and HbC is eluted.

8. The method for determining hemoglobins of claim 1, wherein said eluent further contains at least one type of amine having a molecular weight of 20–500.

9. The method for determining hemoglobins of claim 1, further comprising the use of a hemolyzing reagent containing at least one type of amine having a molecular weight of 20–500.

10. A method for determining hemoglobins by a cation exchange LC comprising the use of an eluent containing a chaotropic ion, at least one type of amine having a molecular weight of 20–500, and further an inorganic acid, an inorganic acid and/or any salt thereof having a buffer capacity in the 4.0–6.8 pH range.

11. A method for determining hemoglobins by a cation exchange LC comprising the use of an eluent containing a chaotropic ion, a buffer agent having acid dissociation constants (pKa) in the range of 2.15–6.39 and in the range of 6.40–10.50, and at least one type of amine having a molecular weight of 20–500.

* * * * *